US008367360B2

(12) United States Patent
Ward et al.

(10) Patent No.: US 8,367,360 B2
(45) Date of Patent: Feb. 5, 2013

(54) METHOD OF SCREENING FOR INHIBITORS OF TAU PROTEIN PHOSPHORORYLATION BY TYROSINE KINASE C-ABL

(75) Inventors: Malcolm Ward, Surrey (GB); Helen Byers, Surrey (GB); Brian Henry Anderton, London (GB); Pascal Derkinderen, London (GB); Christopher Hugh Reynolds, London (GB); Ritchie Williamson, London (GB)

(73) Assignees: Proteome Sciences plc, Surrey (GB); King's College London, London (GB)

( * ) Notice: Subject to any disclaimer, the term of this patent is extended or adjusted under 35 U.S.C. 154(b) by 889 days.

(21) Appl. No.: 11/630,720

(22) PCT Filed: Jun. 21, 2005

(86) PCT No.: PCT/GB2005/002475
§ 371 (c)(1),
(2), (4) Date: Jun. 4, 2007

(87) PCT Pub. No.: WO2005/123048
PCT Pub. Date: Dec. 29, 2005

(65) Prior Publication Data
US 2008/0103107 A1 May 1, 2008

Related U.S. Application Data

(60) Provisional application No. 60/580,901, filed on Jun. 21, 2004.

(51) Int. Cl.
*C12Q 1/48* (2006.01)
(52) U.S. Cl. .......................................................... 435/15
(58) Field of Classification Search .................. None
See application file for complete search history.

(56) References Cited

U.S. PATENT DOCUMENTS
2004/0082639 A1* 4/2004 Ho et al. ........................ 514/405

OTHER PUBLICATIONS

Williamson et al, Rapid tyrosine phosphorylation of neuronal proteins including tau and focal adhesion kinase in response to amyloid-beta peptide exposure: involvement of Src family protein kinases. J Neurosci. Jan. 1, 2002;22(1):10-20.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Tatton et al, The Src-selective kinase inhibitor PP1 also inhibits Kit and Bcr-Abl tyrosine kinases. J Biol Chem. Feb. 14, 2003;278(7):4847-53. Epub Dec. 9, 2002.*
Wu et al, Recognition of multiple substrate motifs by the c-ABL protein tyrosine kinase. Comb Chem High Throughput Screen. Feb. 2002;5(1):83-91.*

Kemp et al, Methods Enzymol. 1991;200:121-34. Design and use of peptide substrates for protein kinases.*
Merriman-Webster, "In vivo" definition. Dec. 12, 2011.*
Lockhart et al, Cognition enhancing or neuroprotective compounds for the treatment of cognitive disorders: why? when? which? Exp Gerontol. Jan.-Feb. 2003;38(1-2):119-28.*
Derkinderen et al., "Tyrosine 394 is phosphorylated i Alzheimer's PHF-tau and in fetal tau with c-Abl being the candidate tyrosine kinase", 7E Colloque de la Societe des neurosciences, May 18-20, 2005, Lille (France), Online! Apr. 26, 2005, XP002350402, Retrieved from the Internet: URL:http://www.neurosciences.asso.fr/activites/colloques/sn05/posters/rl/c_47.html>abstract.
Scales, T. et al., "Tyrosine Phosphorylation of Specific Sites on Tau by SRC Family Kinases", Neurology of Aging, 23(1): S500-S501, (2002).
Lee, Gloria et al., "Phosphorylation of Tau by Fyn: Implications for Alzheimer's Disease", The Journal of Neuroscience, 24(9): 2304-2312 (2004).
Williamson, R. et al., "Rapid Tyrosine Phosphorylation of Neuronal Proteins Including Tau and Focal Adhesion Kinase in Response to Amyloid-B Peptide Exposure: Involvement of Src Family Protein Kinases", Journal of Nueroscience, 22(1): 10-20 (2002).
Gianni, D. et al., "Platelet-derived Growth Factor Induces the B-gamma-secretase-mediated Cleavage of Alzheimer's Amyloid Precursor Protein through a Src-Rac-dependent Pathway", Journal of Biological Chemistry, 278(11): 9290-9297 (2003).
Hanke, J.H. et al., "Discovery of a Novel, Potent, and Src Family-selective Tyrosine Kinase Inhibitor", Journal of Biological Chemistry, 271(20): 695-701 (1996).
Tatton, L. et al., "The Src-selective Kinase Inhibitor PP1 Also Inhibits Kit and BCR-Abl Tyrosine Kinases", Journal of Biological Chemistry, 278(7): 4847-4853 (2003).
Warmuth, M. et al., "Dual-specific Src and Abl kinase inhibitors, PP1 and CGP76030, inhibit growth and survival of cells expressing imatinib mesylate-resistant Bcr-Abl kinases", Blood, 101(2): 664-672 (2003).
Dunah, A.W. et al., "Dopamine D1-Dependent Trafficking of Striatal N-Methyl-D-aspartate Glutamate Receptors Requires Fyn Protein Tyrosine Kinase but Not DARPP-32", Mol. Pharmacol., 65(1): 121-129 (2004).
Eckert, G.P. et al., "Cholesterol Modulates the Membrane-Disordering Effects of Beta-Amyloid Peptides in the Hippocampus: Specific Changes in Alzheimer's Disease", Dementia Geriatr. Cogn. Disord., 11: 181-186 (2000).
Fainstein, E. et al., "Nucleotide sequence analysis of human abl and bcr-abl cDNAs", Oncogene, 4: 1477-1481 (1989).
Girardot, N. et al., "Accumulation of flotillin-1 in tangle-bearing neurones of Alzheimer's disease", Neuropathol. Appl. Neurobiol., 29: 451-461 (2003).
Hanger, D. et al., "New Phosphorylation Sites Identified in Hyperphosphorylated Tau (Paired Helical Filament-Tau) from Alzheimer's Disease Brain Using Nanoelectrospray Mass Spectrometry", J. Neurochem., 71: 2465-2476 (1998).
Lambert, M.P. et al., "Diffusible, nonfibrillar ligands derived from AB1-42 are potent central nervous system neurotoxins", Proc. Natl. Acad. Sci. USA, 95: 6448-6453 (1998).

(Continued)

*Primary Examiner* — Sheridan Swope
(74) *Attorney, Agent, or Firm* — Patrick J. Hagan; Dann, Dorfman, Herrell and Skillman, PC

(57) ABSTRACT

The present invention provides methods of screening for candidate compounds useful in the treatment of Alzheimer's disease and related conditions by inhibiting specific phosphorylation of tau protein by tyrosine kinase c-Abl.

6 Claims, 4 Drawing Sheets

OTHER PUBLICATIONS

Law, C.L. et al., "Molecular Cloning of Human Syk", J. Biol. Chem., 269: 12310-12319 (1994).

Ledesma, M.D. et al., "Raft disorganization leads to reduced plasmin activity in Alzheimer's disease brains", EMBO Reports, 4: 1190-1196 (2003).

Lee, G. et al., "Tau interacts with src-family non-receptor tyrosine kinases", J. of Cell Science, 111: 3167-3177 (1998).

Lee, V.M.Y. et al., "Neurodegenerative Tauopathies", Annu. Rev. Neurosci., 24: 1121-1159 (2001).

Li, S.H. et al., "Lack of Huntingtin-Associated Protein-1 Causes Neuronal Death Resembling Hypothalamic Degeneration in Huntington's Disease", J. Neurosci., 23(17): 6956-6964 (2003).

Liu, T. et al., "Amyloid-B-induced toxicity of primary neurons is dependent upon differentiation-associated increases in tau and cyclin-dependent kinase 5 expression", J. Neurochem., 88: 554-563 (2004).

McDonald, D. et al., "Amyloid Fibrils Activate Tyrosine Kinase-Dependent Signaling and Superoxide Production in Microglia", J. Neurosci., 17(7): 2284-2294 (1997).

Morishima-Kawashima, M. et al., "Proline-directed and Nonproline-directed Phosphorylation of PHF-tau", J. Biol. Chem., 270: 823-829 (1995).

Mulot, S.F.C. et al., "PHF-tau from Alzheimer's brain comprises four species on SDS-PAGE which can be mimicked by in vitro phosphorylation of human brain tau by glycogen synthase kinase-3B", FEBS Lett., 349: 359-364 (1994).

Negro, A., et al., "Multiple phosphoylation of alpha-synuclein by protein tyrosine kinase Syk prevents eosin-induced aggregation", FASEB J., 16: 210-212 (2002).

Rapoport, M. et al., "Tau is essential to B-amyloid-induced neurotoxicity", PNAS, 99: 6364-6369 (2002).

Semba, K. et al., "yes-related protooncogene, syn, belongs to the protein-tyrosine kinase family", Proc. Natl. Acad. Sci. USA, 83: 5459-5463 (1986).

Shirazi, S.K. et al., "The protein tyrosine kinase, fyn, in Alzheimer's disease pathology", Neuroreport, 4: 435-437 (1993).

Subasinghe, S. et al., "Cholesterol is necessary both for the toxic effect of AB peptides on vascular smooth muscle cells and for AB binding to vascular smooth muscle cell membranes", J. Neurochem., 84: 471-479 (2003).

Wang, S.S. et al., "Reduction in Cholesterol and Sialic Acid Content Protects Cells from the Toxic Effects of B-Amyloid Peptides", J. Biol. Chem., 276: 42027-42034 (2001).

Yip, C.M. et al., "Cholesterol, a Modulator of Membrane-associated AB-fibrillogenesis and Neurotoxicity", J. Mol. Biol., 311: 723-734 (2001).

Zukerberg, L.R. et al., "Cables Links Cdk5 and C-Abl and Facilitates Cdk5 Tyrosine Phosphorylation, Kinase Upregulation, and Neurite Outgrowth", Neuron, 26: 633-646 (2000).

* cited by examiner

Fig 1

```
  1  MAEPRQEFEV MEDHAGTYGL GDRKDQGGYT MHQDQEGDTD AGLKESPLQT
 51  PTEDGSEEPG SETSDAKSTP TAEDVTAPLV DEGAPGKQAA AQPHTEIPEG
101  TTAEEAGIGD TPSLEDEAAG HVTQARMVSK SKDGTGSDDK KAKGADGKTK
151  IATPRGAAPP GQKGQANATR IPAKTPPAPK TPPSSGEPPK SGDRSGYSSP
201  GSPGTPGSRS RTPSLPTPPT REPKKVAVVR TPPKSPSSAK SRLQTAPVPM
251  PDLKNVKSKI GSTENLKHQP GGGKVQIINK KLDLSNVQSK CGSKDNIKHV
301  PGGGSVQIVY KPVDLSKVTS KCGSLGNIHH KPGGGQVEVK SEKLDFKDRV
351  QSKIGSLDNI THVPGGGNKK IETHKLTFRE NAKAKTDHGA EIVYKSPVVS
401  GDTSPRHLSN VSSTGSIDMV DSPQLATLAD EVSASLAKQG L
```

Fig 2

```
   1  MLEICLKLVG CKSKKGLSSS SSCYLEEALQ RPVASDFEPQ GLSEAARWNS
  50  KENLLAGPSE NDPNLFVALY DFVASGDNTL SITKGEKLRV LGYNHNGEWC
 101  EAQTKNGQGW VPSNYITPVN SLEKHSWYHG PVSRNAAEYL LSSGINGSFL
 151  VRESESSPGQ RSISLRYEGR VYHYRINTAS DGKLYVSSES RFNTLAELVH
 201  HHSTVADGLI TTLHYPAPKR NKPTVYGVSP NYDKWEMERT DITMKHKLGG
 251  GQYGEVYEGV WKKYSLTVAV KTLKEDTMEV EEFLKEAAVM KEIKHPNLVQ
 301  LLGVCTREPP FYIITEFMTY GNLLDYLREC NRQEVNAVVL LYMATQISSA
 351  MEYLEKKNFI HRDLAARNCL VGENHLVKVA DFGLSRLMTG DTYTAHAGAK
 401  FPIKWTAPES LAYNKFSIKS DVWAFGVLLW EIATYGMSPY PGIDLSQVYE
 451  LLEKDYRMER PEGCPEKVYE LMRACWQWNP SDRPSFAEIH QAFETMFQES
 501  SISDEVEKEL GKQGVRGAVS TLLQAPELPT KTRTSRRAAE HRDTTDVPEM
 551  PHSKGQGESD PLDHEPAVSP LLPRKERGPP EGGLNEDERL LPKDKKTNLF
 601  SALIKKKKKT APTPPKRSSS FREMDGQPER RGAGEEEGRD ISNGALAFTP
 651  LDTADPAKSP KPSNGAGVPN GALRESGGSG FRSPHLWKKS STLTSSRLAT
 701  GEEEGGGSSS KRFLRSCSAS CVPHGAKDTE WRSVTLPRDL QSTGRQFDSS
 751  TFGGHKSEKP ALPRKRAGEN RSDQVTRGTV TPPPRLVKKN EEAADEVFKD
 801  IMESSPGSSP PNLTPKPLRR QVTVAPASGL PHKEEAEKGS ALGTPAAAEP
 851  VTPTSKAGSG APGGTSKGPA EESRVRRHKH SSESPGRDKG KLSRLKPAPP
 901  PPPAASAGKA GGKPSQSPSQ EAAGEAVLGA KTKATSLVDA VNSDAAKPSQ
 951  PGEGLKKPVL PATPKPQSAK PSGTPISPAP VPSTLPSASS ALAGDQPSST
1001  AFIPLISTRV SLRKTRQPPE RIASGAITKG VVLDSTEALC LAISRNSEQM
1051  ASHSAVLEAG KNLYTFCVSY VDSIQQMRNK FAFREAINKL ENNLRELQIC
1101  PATAGSGPAA TQDFSKLLSS VKEISDIVQR
```

Fig 3

```
  1    MASSGMADSA  NHLPFFFGNI  TREEAEDYLV  QGGMSDGLYL  LRQSRNYLGG
 51    FALSVAHGRK  AHHYTIEREL  NGTYAIAGGR  THASPADLCH  YHSQESDGLV
101    CLLKKPFNRP  QGVQPKTGPF  EDLKENLIRE  YVKQTWNLQG  QALEQAIISQ
151    KPQLEKLIAT  TAHEKMPWFH  GKISREESEQ  IVLIGSKTNG  KFLIRARDNN
201    GSYALCLLHE  GKVLHYRIDK  DKTGKLSIPE  GKKFDTLWQL  VEHYSYKADG
251    LLRVLTVPCQ  KIGTQGNVNF  GGRPQLPGSH  PATWSAGGII  SRIKSYSFPK
301    PGHRKSSPAQ  GNRQESTVSF  NPYEPELAPW  AADKGPQREA  LPMDTEVYES
351    PYADPEEIRP  KEVYLDRKLL  TLEDKELGSG  NFGTVKKGYY  QMKKVVKTVA
401    VKILKNEAND  PALKDELLAE  ANVMQQLDNP  YIVRMIGICE  AESWMLVMEM
451    AELGPLNKYL  QQNRHVKDKN  IIELVHQVSM  GMKYLEESNF  VHRDLAARNV
501    LLVTQHYAKI  SDFGLSKALR  ADENYYKAQT  HGKWPVKWYA  PECINYYKFS
551    SKSDVWSFGV  LMWEAFSYGQ  KPYRGMKGSE  VTAMLEKGER  MGCPAGCPRE
601    MYDLMNLCWT  YDVENRPGFA  AVELRLRNYY  YDVVN
```

Fig 4

```
1    MGCVQCKDKE  ATKLTEERDG  SLNQSSGYRY  GTDPTPQHYP  SFGVTSIPNY
51   NNFHAAGGQG  LTVFGGVNSS  SHTGTLRTRG  GTGVTLFVAL  YDYEARTEDD
101  LSFHKGEKFQ  ILNSSEGDWW  EARSLTTGET  GYIPSNYVAP  VDSIQAEEWY
151  FGKLGRKDAE  RQLLSFGNPR  GTFLIRESET  TKGAYSLSIR  DWDDMKGDHV
201  KHYKIRKLDN  GGYYITTRAQ  FETLQQLVQH  YSERAAGLCC  RLVVPCHKGM
251  PRLTDLSVKT  KDVWEIPRES  LQLIKRLGNG  QFGEVWMGTW  NGNTKVAIKT
301  LKPGTMSPES  FLEEAQIMKK  LKHDKLVQLY  AVVSEEPIYI  VTEYMNKGSL
351  LDFLKDGEGR  ALKLPNLVDM  AAQVAAGMAY  IERMNYIHRD  LRSANILVGN
401  GLICKIADFG  LARLIEDNEY  TARQGAKFPI  KWTAPEAALY  GRFTIKSDVW
451  SFGILLTELV  TKGRVPYPGM  NNREVLEQVE  RGYRMPCPQD  CPISLHELMI
501  HCWKKDPEER  PTFEYLQSFL  EDYFTATEPQ  YQPGENL
```

METHOD OF SCREENING FOR INHIBITORS OF TAU PROTEIN PHOSPHORORYLATION BY TYROSINE KINASE C-ABL

CROSS-REFERENCE TO RELATED APPLICATIONS

This application is the U.S. National Stage of International Application No. PCT/GB2005/002475, filed Jun. 21, 2005, which claims priority from U.S. Provisional Application No. 60/580,901, filed Jun. 21, 2004. The disclosures of the aforesaid applications are incorporated by reference in their entireties in the present application.

FIELD OF THE INVENTION

The present invention relates to screening methods, and more particularly to methods which relate to the role of tyrosine kinases as therapeutic targets for Alzheimer's disease and related conditions.

BACKGROUND OF THE INVENTION

Alzheimer's disease (AD) is a neurodegenerative disease characterised by the presence of senile plaques and neurofibrillary tangles in the brain. The degree of dementia at death correlates better with neurofibrillary tangle numbers and with neuronal and synaptic loss than with senile plaque counts. The presence of neurofibrillary tangles in neurons results in the death of those neurons, implying that prevention of tangle formation is an important therapeutic goal. The principal protein that forms the neurofibrillary tangle is the microtubule-associated protein, tau, which assembles into filaments that have the appearance of twisting about each other in pairs and are referred to as paired helical filaments (PHF). PHF are present in different locations in degenerating neurons in the Alzheimer brain and when many aggregate in the neuronal cell body, they produce the neurofibrillary tangle (Lee et al., 2001).

Senile plaques have an extracellular central deposit of amyloid β-peptide (Aβ), which is surrounded by dystrophic neurites to form the senile or neuritic plaque. In vitro and in vivo Aβ has been shown to be neurotoxic. Aβ is derived by proteolytic processing of the larger amyloid precursor protein (APP). Much attention has been focused on Aβ production as a therapeutic target because its production is believed to be an early event in AD pathogenesis. This is because mutations in the APP gene, which give rise to autosomal dominant AD, result in either increased overall production of Aβ or in a relative increase in the slightly longer $A\beta_{42}$ over $A\beta_{40}$, the former being more amyloidogenic; $A\beta_{42}$ has two additional hydrophobic amino acids at the C-terminus of 40-residue $A\beta_{40}$ thereby endowing the peptide with an increased tendency to aggregate and form amyloid fibres. Mutations in two other genes that also cause autosomal dominant AD, presenilin-1 and presenilin-2 (PS1 & PS2) also result in an increase in the ratio of $A\beta_{42}$ to $A\beta_{40}$. The belief that Aβ deposition in the brain precedes the appearance of neurofibrillary tangles has been the basis of the amyloid cascade hypothesis but it has been uncertain whether tangles are important in pathogenesis or are only an unimportant epiphenomenon. This has been changed by the discovery of mutations in the gene for tau in some other related neurodegenerative diseases.

The mechanism by which Aβ kills neurons in the brain has still to be established. Many studies of Aβ toxicity have been conducted in tissue culture using rat brain neuronal cultures. We have shown that exposure of both foetal rat and human brain neuronal cultures to aggregated Aβ induces within 2 to 10 minutes increases in the phosphotyrosine content of several proteins including tau (Williamson et al., 2002). We have also shown that this treatment results in activation of the tyrosine kinases FAK and Fyn, the latter being a member of the src family of tyrosine kinases. This tyrosine phosphorylation of tau was prevented by inhibitors that act on the src family of tyrosine kinases and act on c-Abl.

It has previously been reported that increased levels of Fyn are associated with neurons containing abnormally phosphorylated tau in AD brain (Shirazi and Wood, 1993) and we have demonstrated using antibodies that recognise phosphotyrosine that PHF-tau from AD brain contains phosphotyrosine (Williamson et al., 2002). There are five potential sites for tyrosine phosphorylation in tau, these are residues 18, 29, 197, 310 and 394, based upon the numbering of residues in the longest human brain isoforms of tau of 441 amino acids. We have shown in vitro that Fyn and Lck, both src family kinases, phosphorylate recombinant human tau and phosphotyrosines 18, 197, 310 and 394 were positively identified in one or more of their respective tryptic peptides, from sequence information of fragmented peptides (Scales et al., 2002).

Neurons in brain slices from transgenic mice in which the Fyn gene has been disrupted are resistant to Aβ toxicity (Lambert et al., 1998). Thus, there is evidence that activation of Fyn may be involved in Aβ toxicity.

It has been reported that Aβ treatment of microglia in culture results in activation of several other tyrosine kinases, namely Syk, Lyn and FAK (McDonald et al., 1997) and, as mentioned above, we have found that FAK is also activated in primary neurons exposed to Aβ (Williamson et al., 2002). Syk has been reported to phosphorylate α-synuclein on tyrosine, α-synuclein being the principal protein of Lewy bodies which are the pathological hallmark of Parkinson's disease and are also present in up to 70% of AD brains (Negro et al., 2002). Finally, we have found that the protein tyrosine kinase Abl phosphorylates tau in co-transfected cells and Abl is implicated in activation of the serine/threonine protein kinase cdk5, which is regarded as a pathogenically important tau kinase that phosphorylates many residues in tau that can alternatively be phosphorylated by GSK-3 (Zukerberg et al., 2000). Thus, there is the strong possibility that tau is a substrate for various tyrosine kinases and that these need to be considered in the context of the possible pathogenesis of the tauopathies.

The presence of intraneuronal deposits of tau in the form of typical neurofibrillary tangles in AD or other morphologically distinct tau aggregates in a number of other neurodegenerative diseases, is the basis for grouping these conditions as tauopathies. Thus, in addition to AD, the main examples of the tauopathies are frontotemporal dementia with Parkinsonism linked to chromosome 17 (FTDP-17), progressive supranuclear palsy (PSP), Pick's disease, corticobasal degeneration, and multisystem atrophy (MSA). The intracellular tau deposits (usually neuronal but sometimes also glial) are filamentous and in a hyperphosphorylated state compared to the phosphorylation of tau in control human brain. In the case of AD, this hyperphosphorylated tau is often referred to as PHF-tau because it is derived from the PHF.

Other than for AD, deposits of Aβ in the brain are either absent or minimal in these other tauopathies. There are some tauopathy pedigrees with autosomal dominant disease in which the causative gene has been identified as the tau gene and although cases with the same mutation may present with apparently different diseases, they invariably have tau deposits in the brain and are mostly of the FTDP-17 variety. Thus, the finding of mutations in the tau gene which result in disease and deposition of tau aggregates in neurons is compelling evidence for the primary pathogenic importance of tau deposition in all of these conditions, including AD, whatever the primary cause of disease. Therefore, the amyloid cascade hypothesis is borne out by the discovery of tau mutations and confirms that indeed neurofibrillary tangle formation may well be subservient to Aβ deposition in AD, but that in the other tauopathies lacking Aβ deposits, then some other primary event must trigger the tau pathology. Tau abnormalities and deposition are therefore important therapeutic targets for all tauopathies, including AD.

Tau is a phosphoprotein, the function of its phosphorylation remaining to be unequivocally established. However, increased phosphorylation of tau on multiple serine and threonine residues reduces the ability of tau to promote microtubule assembly and to stabilise assembled microtubules, effects that have been demonstrated both in vitro and in cells. Many studies have shown that PHF-tau from AD brain is more heavily phosphorylated on serine and threonine than tau from control brain. This has been demonstrated partly by protein sequencing and partly by demonstrating that certain monoclonal antibodies only label either PHF-tau or alternatively they label non-phosphorylated tau and not PHF-tau; the epitopes for many of these antibodies have been mapped to particular phosphorylated residues present in PHF-tau and absent from, or present at lower levels in, control brain tau. The pathological tau from most other cases of other tauopathies seems to be similarly hyperphosphorylated to PHF-tau.

These findings strongly imply that similar abnormalities in regulating phosphorylation of tau are shared by all the tauopathies including AD. Since phosphorylation of proteins is effected by protein kinases and dephosphorylation by protein phosphatases, identifying the protein kinases and phosphatases for tau is important because these enzymes are potential therapeutic targets for these diseases.

As mentioned above, there are five tyrosines in human brain tau. It has been reported that Fyn phosphorylates tau in non-neuronal co-transfected cells and that tyrosine 18 is the preferred phosphorylation site (Lee et al., 1998). We have reported that PHF-tau isolated from Alzheimer brain is phosphorylated on tyrosines and others have identified tyrosine 18 as one site of phosphorylation (Williamson et al., 2002; Lee et al., 2004).

Cultured neurons from transgenic mice in which the tau gene has been disrupted, such that these animals no longer express the tau protein, are resistant to exposure to Aβ and do not die (Rapoport et al., 2002). This requirement of tau for Aβ to be neurotoxic has been confirmed in experiments in which neurons treated with antisense oligonucleotides to reduce expression of tau were resistant to the neurotoxic effects of Aβ exposure (Liu et al., 2004).

It remains a considerable problem in the art in identifying the enzymes responsible for causing phosphorylation of paired helical filament tau and the sites phosphorylated by those enzymes.

SUMMARY OF THE INVENTION

Broadly, the present invention relates to the modulation of the phosphorylation of tau protein at tyrosine sites through its interaction with kinases. In particular, the present invention concerns the identification of tyrosine phosphorylation sites in tau protein and the kinases that preferentially phosphorylate subsets of those sites (e.g. tyrosine kinases). This identifies novel therapeutic targets and interactions that can be employed in methods of screening for candidate therapeutic agents. In one aspect, the present invention is based on the identification of the role played by the protein tyrosine kinase c-Abl in the phosphorylation of tyrosine 394 in PHF tau. This has not previously been disclosed in the prior art. Prior to the present invention, the prior art proposed that tyrosine 394 was phosphorylated by Fyn, another Src family protein tyrosine kinase. Thus, in contrast to prior art approaches based on screening for compounds capable of inhibiting tyrosine 394 phosphorylation by inhibition of Fyn kinase, in one aspect, the present invention provides methods of screening for substances useful in the treatment of AD, or another tauopathy, which are inhibitors of c-Abl.

Some of the work described herein involved the technically difficult determination of tau phosphorylation state in PHF tau from Alzheimer's patients brains, rather than more conventional approaches employing normal tau or fetal brain tau. Accordingly, the present invention provides the first disclosure of the presence of tyrosine phosphorylation in clinical PHF tau, and in some aspects, the first to link a specific kinase with a specific phosphorylation event.

Furthermore, the identification herein of c-Abl as a candidate for a target to treat AD is based on modifying the disease associated tyrosine phosphorylation of tau and is further supported by the observation that c-Abl may be a source of cdk5 activation since cdk5 is proposed as an alternative to GSK-3 in the production of PHF tau.

Furthermore, the present invention proposes that fyn, lck and c-Abl are candidate targets for drugs to treat AD or other tauopathies because of the work described herein which links these kinases to the amyloid cascade theory through their recruitment to lipid rafts. Without wishing to be bound by any particular explanation, the present inventors propose that Aβ activates these tyrosine kinases through interaction with cholesterol-rich domains of cell membranes and that this results in an inappropriate over-association of tau with these regions of membranes and a subsequent disturbance of intracellular cell signalling processes. The kinases involved in these signalling events can therefore be used alone or in any combination as therapeutic targets for the screening of modulators of the activity and/or their interaction with tau.

Accordingly, the present invention provides methods of screening for candidate compounds useful in the treatment of Alzheimer's disease or a tauopathy that act by inhibiting specific phosphorylation of tau protein. These methods can be carried out in many ways including measurement by mass spectrometry and immunoassay.

Considering the requirements described above for the obligatory expression of both Fyn and tau in order for Aβ to be neurotoxic and the previously known fact that Fyn can phosphorylate tau in cells, the present inventors propose that a sequence of biochemical events is involved in the processing of tau. This is that exposure of neurons to Aβ induces activation of Fyn and probably other protein tyrosine kinases, which then phosphorylates tau and this results in a series of further biochemical changes ending in neuronal cell death, which may involve hyperphosphorylation of tau on numerous serine and threonine residues.

The first stage in identifying the responsible enzymes is to map all of the phosphorylation sites in PHF-tau and compare the complement of sites with those in control brain tau. Protein sequencing studies have in total resulted in the identification of 25 phosphorylation sites in PHF-tau (Hanger et al., 1998; Morishima-Kawashima et al., 1995); control brain tau has not been studied as extensively and only a few of these sites have been identified in tau from adult control human brain or from foetal control human brain (tau from foetal brain is known to be more phosphorylated than that from adult brain).

As described above, the prior art disclosed that of the five potential tyrosine phosphorylation sites present in human tau protein at positions 18, 29, 197, 310 and 394, the tyrosine kinases Lck and Fyn phosphorylate tau at tyrosine positions 18, 310 and 394 and that tyrosine 18 is the preferred phosphorylation site of Fyn. However, the present invention discloses for the first time that PHF-tau from AD brain is phosphorylated at Tyr-394, a new result arising from mass spectrometry experiments. The present invention also demonstrates that Fyn phosphorylates primarily Tyr-18 in cells, and that Abl phosphorylates primarily Tyr-394. These findings mean that the phosphorylation of Tyr-394 may contribute to AD pathology and that Abl is a potential drug target.

Accordingly, the work described in the present application refines the initial indications provided in the prior art and to investigate how Aβ may trigger activation of Fyn, how Fyn might come into contact with tau, and on which particular tyrosine residues in tau Fyn, and the kinases Syk and Abl, might act.

Aβ Neurotoxicity—Lipid Rafts

Fyn is known to be associated with lipid rafts, which are domains of cell membranes rich in cholesterol and sphingolipids. Solubilising cells in certain detergents such as Triton X100 at 4° C. enables isolation of lipid rafts since these cholesterol-rich domains remain insoluble and can be separated from other cell components by virtue of their low buoyant density. Thus, lipid rafts are isolated by flotation on sucrose solutions by ultracentrifugation. Furthermore, it has been reported that binding of Aβ to membranes is mediated, at least in part, by cholesterol and that increasing membrane cholesterol levels is positively correlated with Aβ toxicity to neuronal and endothelial cells (Eckert et al., 2000; Subasinghe et al., 2003; Wang et al., 2001; Yip et al., 2001). Flotillin, a lipid raft constituent, accumulates in tangle-bearing neurons in Alzheimer brain indicating abnormalities in lipid rafts in the diseased brain (Girardot et al., 2003), and indeed the protein composition of lipid rafts isolated from Alzheimer brain has been reported to be abnormal (Ledesma et al., 2003). We have investigated lipid rafts in the context of Aβ neurotoxicity.

The present application describes investigations into the effects on lipid rafts of exposing neurons to Aβ. To summarise, we have found by western blotting that lipid rafts isolated from primary cultures of rat brain cortical neurons contain the marker protein, flotillin, as well as Fyn, FAK, and small but reproducible amounts of actin, tubulin and tau. After exposure to 10 μM Aβ for 5 min, there is an increase in the phosphotyrosine content of numerous proteins, as detected with the phosphotyrosine monoclonal antibody 4G10; there are also increases in the amounts of Fyn, FAK, tau, tubulin, actin and c-Src kinase, but not β-catenin, relative to the flotillin content of lipid rafts compared to untreated neurons.

We have also found that pre-treatment of neuronal cultures with the Src family tyrosine kinase inhibitor, PP2, before exposure to Aβ and subsequent isolation of lipid rafts, resulted in blocking of the recruitment of increased quantities of tau and Fyn to the lipid rafts that was induced by Aβ.

Tyrosine Phosphorylation of Tau

Fyn has previously been shown to phosphorylate tau in cells co-transfected with tau and Fyn (Lee et al., 1998). As mentioned above, we previously found that in vitro Fyn and Lck phosphorylate human tau on four of the five tyrosines present in human tau (Y18, Y197, Y310, Y394) (Scales et al., 2002). We have now made a series of mutant forms of tau in which either each of the five tyrosines was individually mutated to phenylalanine (F18, F29, F197, F310, F394) or in which only a single tyrosine remained with the other four replaced by phenylalanine (Y18-only, Y29-only, Y197-only, Y310-only, Y394-only).

Using these mutants, we have found that by treating non-neuronal cells transfected with these mutant forms of tau with pervanadate to inhibit tyrosine phosphatases, there is an increase in endogenous tyrosine phosphorylation of tau, principally on tyrosine 394 with a contribution from tyrosine 197. In other experiments in which mutant forms of tau were co-transfected with Fyn, Syk or Abl tyrosine kinases, we found preferential phosphorylation of tyrosine 18 and 310 by Fyn, tyrosines 18, 29, 197 and 394 by Syk but Abl phosphorylated preferentially tyrosines 197, 310 and 394.

Using rat brain lysate in the presence of pervanadate to phosphorylate recombinant human tau in vitro, we have found by mass spectrometry that tyrosines 310 and 394 were phosphorylated.

Finally, tyrosine phosphorylation in tau is a physiological event since we have found by mass spectrometry unequivocal evidence that tyrosine 394 is phosphorylated in tau isolated from human foetal brain and in PHF.

Tyrosine Phosphorylation of Tau Generates an SH2 Binding Site for Fyn

We have found that in vitro phosphorylation of tau by Lck generates a binding site for the SH2 domain of Fyn. In summary, the evidence suggests that more than one tyrosine kinase phosphorylates tau, with different kinases preferentially phosphorylating different tyrosine residues, and that Aβ is capable of activating at least some of these kinases. The data also demonstrate that tyrosine phosphorylation of tau generates a binding site for at least one tyrosine kinase, implying that tau may be an important cell signalling protein in addition to its role as a microtubule-associated protein.

Accordingly, in one aspect, the present invention proposes that three kinases phosphorylate tau protein at the tyrosine phosphorylation sites at Tyr18, Tyr29, Tyr197, Tyr310 and Tyr394. The kinases are Fyn, Syk and Abl. A description and the sequences of these kinases are provided in:

Fyn: Semba, K. et al (1986) Proc. Natl. Acad. Sci. USA 83, 5459-5463. See Genbank NM_002037 and that there are two main isoforms. The present invention is primarily concerned with the isoform expressed in brain, but the other isoform expressed in haematopoietic cells, such as T cells, may also find use in the method of screening disclosed herein.

Syk: Law, C. L. et al, J. Biol. Chem. 269, 12310-12319. See Genbank L28824.

c-Abl: Fainstein, E., Einat, M., Gokkel, E., Marcelle, C., Croce, C. M., Gale, R. P. and Canaani, E. (1989) Oncogene 4, 1477-1481. See Genbank X16416 and M14752. There are several isoforms involving the N-terminus, but having a similar catalytic domain.

In referring to these kinases, the present invention includes the use of isoforms, splice variants, fragments and sequence variants, as discussed in more detail below.

In particular, the kinases and the sites they preferentially phosphorylate can be used in methods of screening for inhibitors of phosphorylation or promoters of dephosphorylation. Preferably, the screening method is for finding substances which are capable of inhibiting phosphorylation. The screening method may involve determining whether a candidate substance is capable of binding to the kinase and/or tau protein, e.g. to inhibit or prevent the phosphorylation of tau protein at a given site by the kinase in question. This method may involve contacting the candidate substance with the kinase and/or tau protein and determining whether binding occurs, and optionally the affinity of the binding reaction. Alternatively or additionally, the method may comprise determining whether a candidate substance is capable of inhibiting a kinase, e.g. to inhibit or prevent the phosphorylation of a substrate such as a tau protein at a site by one of the kinases, as disclosed herein. This determination may comprise contacting a candidate substance with the kinase in question and tau protein or an alternative substrate (e.g. a fragment of tau comprising the amino acid sequence around the phosphorylation site), and determining whether the candidate substance inhibits the kinase phosphorylating the substrate. The determining step may comprise determining the extent of the inhibition. In situations where an initial screen is carried out to identify candidate substances which are capable of binding to tau protein or a kinase, or are capable of inhibiting the activity of a kinase, the method may comprise the further step of determining whether the binding or inhibiting property of the candidate substance is capable of inhibiting the phosphorylation of tau protein or a fragment thereof in the presence of the kinase.

The screening for candidate substances having these properties may employ tau protein, or a fragment, active portion or sequence variant thereof comprising one or more of the relevant phosphorylation sites. One example of a tau protein that may be employed in this way is a fragment of tau comprising the amino acid sequence around the phosphorylation site.

The sites and the kinases that preferentially phosphorylate them are tyrosines 18 and 310 by Fyn, tyrosines 18, 29, 197 and 394 by Syk, and tyrosines 197, 310 and 394 by Abl.

As a consequence of these findings, the new sites and kinases can be used as the basis of assays and assays methods for screening for modulators of the phosphorylation of the sites in tau protein for use or development as therapeutics for the treatment of tauopathies. As a first step, the candidate substances may be tested to determine whether they are inhibitors or promoters of the kinases disclosed herein. Optionally, the method may alternatively or additionally comprise determining whether a candidate substance is capable of inhibiting the phosphorylation of tau by a kinase and/or promoting the dephosphorylation of phosphorylated tau by a phosphatase (e.g. a tyrosine phosphatase).

Accordingly, in a further aspect, the present invention provides the use of (a) a kinase which is capable of phosphorylating tau protein at the one or more of the sites disclosed herein and (b) a substrate of the kinase, wherein the kinase and substrate are used for identifying candidate substances which are capable of inhibiting phosphorylation of the substrate by a kinase.

In the present invention, the tau protein comprising the phosphorylation sites may be substantially full length and/or wild type tau or PHF tau protein, or may be a fragment, active portion or sequence variant thereof. In other embodiments, the present invention may employ a corresponding nucleic acid molecule encoding the tau protein. Where a tau protein which is a fragment, active portion or sequence variant is employed, the phosphorylation site(s) may be present with surrounding amino acids from the tau protein sequence. Preferably, the present invention employs PHF tau protein. In the present invention the numbering of tau and PHF tau is according to the sequence disclosed FIG. 1 of Goedert et al (1989) Neuron 3, 519-526: Multiple isoforms of human microtubule-associated protein Tau: sequences and localisation in neurofibrillary tangles of Alzheimer's Disease Goedert M, Spillantini M G, Rutherford D, Jakes R and Crowther R A.

Alternatively or additionally, any of the above defined tau proteins may possess phosphorylation at one or more of the phosphorylation sites. This enables the effects of cooperative phosphorylation of the protein to be studied, that is, where the phosphorylation of one site is dependent in changes to the tau protein caused by one or more preceding or simultaneous phosphorylation steps. Thus, in some embodiments of the present invention, the tau protein may include one or more of the known tau phosphorylation sites.

In a further aspect, the present invention provides a method of screening for substances which are capable of inhibiting phosphorylation at one or more of the site(s) of a substrate by a kinase, the method comprising:
(a) contacting at least one candidate substance, a kinase which is capable of phosphorylating tau protein at the one or more of the sites disclosed herein and a substrate of the kinase;
(b) determining whether, and optionally the extent to which, the candidate substance inhibits the phosphorylation of the substrate by the kinase; and,
(c) selecting the candidate substance which inhibits phosphorylation of the substrate.

The method disclosed herein may be employed for identifying candidate substances useful in treating or developing lead compounds for treating tauopathies.

In all aspects of the invention, the substrate may be a tau protein, or comprise a fragment of tau protein, which includes one or more of the phosphorylation site(s) acted on by the kinase. For example, in the case of c-Abl, the substrate may be a fragment of tau protein based on the amino acid sequence surrounding Tyr 394. However, in other embodiments, other non-tau based substrates of the kinase may be employed, for example where a substrate of the kinase is readily available. In this case, the method may comprise the further step of confirming whether a candidate substance selected in an initial screen has the property of inhibiting the phosphorylation of the tau protein under conditions in which the kinase is capable of phosphorylating the site(s) of the tau protein in the absence of the candidate substance.

In this embodiment, the method may additionally involve including a phosphatase inhibitor in step (a) to inhibit phosphatases that may be present in the system from dephosphorylating the tau protein.

In a further aspect, the present invention provides a method of screening for substances which are capable of promoting dephosphorylation at one or more of the site(s) of a substrate by a phosphatase, the method comprising:
(a) contacting at least one candidate substance, a phosphatase which is capable of dephosphorylating tau protein at the one or more of the sites disclosed herein and a substrate of the phosphatase;
(b) determining whether, and optionally the extent to which, the candidate substance promotes the dephosphorylation of the substrate by the phosphatase; and,
(c) selecting the candidate substance which promotes the dephosphorylation of the substrate.

In this embodiment, the method may additionally involve including a kinase inhibitor in step (a) to inhibit kinases that may be present in the system from phosphorylating the tau protein.

Examples of screening techniques suitable for use according to the present invention will be well known to the skilled person. By way of example, a cell based screening assay may be carried out by co-transfecting cells with nucleic acid encoding tau and encoding one or more of Fyn, Syk or Abl tyrosine kinases, and determining the effect that candidate compounds have on tau phosphorylation, in particular at tyrosines 18 and 310 by Fyn, tyrosines 18, 29, 197 and 394 by Syk and tyrosines 197, 310 and 394 by Abl. Preferred methods of screening may involve the use of mass spectroscopy to determine the phosphorylation at sites of tau, and this is described in detail below. Conveniently, the methods of screening may be carried out in a multiplex assay format in which a solid phase is employed on which a plurality of substrates are immobilised (e.g. in an array), the substrates corresponding to phosphorylation sites of tau. By way of example, the substrates may comprise fragments of tau protein. This is described in more detail below. The present invention therefore provides a kit or solid phase adapted for carrying out a multiplex screening assay according to the present invention.

In some embodiments, the method may comprise, having identified a candidate substance according to one of the methods disclosed herein, the further step(s) of optimising the candidate substance to improve one or more of its properties and/or formulating it as a pharmaceutical.

The methods and uses disclosed herein employ one of more kinases selected from Fyn, Syk or Abl. However, the screening method may comprise investigating the effect of one or more further enzymes on phosphorylation sites of tau. Examples of suitable further enzymes for use in any aspect of the invention are provided below in the section on multiplex assays.

In a further aspect, the invention provides for the use of a modulator of tau protein phosphorylation obtainable by the methods described herein in the treatment of a tauopathy. Preferably, the modulator is an inhibitor of tau protein phosphorylation.

In a related aspect, the invention provides for the use of a c-Abl, Syk or Fyn inhibitor in the preparation of a medicament for the treatment of a tauopathy.

In the present invention, preferably the step of detecting the presence and extent of phosphorylation and dephosphorylation in the tau protein can be carried out using mass spectroscopy as described in detail below. Alternatively, or additionally, site specific recognition agents which are capable of distinguishing between a site which is phosphorylated and one which is not may be used. Examples of such agents known in the art are site specific antibodies such as monoclonal antibody AT100.

In a further aspect, the present invention provides a substance obtainable from one of the methods disclosed herein which is capable of inhibiting the phosphorylation or promoting the dephosphorylation of a tau protein at one or more of the above defined sites.

BRIEF DESCRIPTION OF THE FIGURES

FIG. 1 shows the amino acid sequence of the human tau isoform used for the numbering given in this application (SEQ ID NO: 1). The phosphorylation sites Y18, Y29, Y197, Y310 and Y394 are indicated in bold.

FIG. 2 shows the amino acid sequence of the p150 isoform of human c-Abl (SEQ ID NO: 2).

FIG. 3 shows the amino acid sequence of human Syk (SEQ ID NO: 3).

FIG. 4 shows the amino acid sequence of isoform 1 of human Fyn (SEQ ID NO: 4).

Embodiments of the present invention will now be discussed in more detail by way of example and not limitation.

DETAILED DESCRIPTION

Tau Proteins

The assays and assay methods disclosed herein can employ wild-type or full length tau proteins, kinases or phosphatases or fragments, active portions or derivatives thereof. In the case of tau proteins, the materials used in the assays may be unphosphorylated or partially phosphorylated as discussed above.

In the present invention, derivatives of the tau proteins, kinases (especially Fyn, Syk and Abl) or phosphatases have an amino acid sequence which differs by one or more amino acid residues from the wild-type amino acid sequence, by one or more of addition, insertion, deletion and substitution of one or more amino acids. Thus, variants, derivatives, alleles, mutants and homologues, e.g. from other organisms, are included. Thus, a derivative of tau protein or kinase may include 1, 2, 3, 4, 5, greater than 5, or greater than 10 amino acid alterations such as substitutions with respect to the wild-type sequence.

Preferably, a fragment or derivative of a protein used in the assays disclosed herein shares sequence identity with the corresponding portion of the relevant wild-type sequence of the protein, and preferably has at least about 60%, or 70%, or 75%, or 80%, or 85%, 90% or 95% sequence identity. Preferred fragments comprise at least 5, at least 10, at least 15, at least 20 or at least 25 amino acids which correspond to or share sequence identity with tau protein. Optionally, the fragments may comprise a fragment of tau protein linked or conjugated to other moieties, for example expression tags, purification tags, groups to enable the fragment to be immobilised or otherwise manipulated, or labels. As is well-understood, identity at the amino acid level is generally in terms of amino acid identity which may be defined and determined by the TBLASTN program, of Altschul et al. (1990) *J. Mol. Biol.* 215: 403-10, which is in standard use in the art. Identity may be over the full-length of the relevant peptide or over a contiguous sequence of about 5, 10, 15, 20, 25, 30, 35, 50, 75, 100 or more amino acids, compared with the relevant wild-type amino acid sequence. Alternatively, nucleic acid encoding a fragment or derivative may hybridise to the corresponding wild type nucleic acid under stringent conditions, for example as disclosed in textbooks such as Ausubel, Short Protocols in Molecular Biology, 1992 or Sambrook et al, Molecular Cloning, A Laboratory Manual, Cold Spring Harbour Laboratory Press, 1989, using a hybridization solution comprising: 5×SSC, 5× Denhardt's reagent, 0.5-1.0% SDS, 100 μg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5° C. + 16.6 \text{ Log } [Na+] + 0.41 \text{ (\% G+C)} - 0.63$$
$$(\text{\% formamide}) - 600/\text{\#bp in duplex}.$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Methods of Screening for Inhibitors and Enhancers

It is well known that pharmaceutical research leading to the identification of a new drug may involve the screening of very large numbers of candidate substances, both before and even after a lead compound has been found. This is one factor which makes pharmaceutical research very expensive and time-consuming. Means for assisting in the screening process can have considerable commercial importance and utility.

As detailed above, methods of screening for a substance which are inhibitors of phosphorylation of tau protein or promoters of dephosphorylation of tau protein can be carried out by contacting one or more test substances with the tau protein and kinase or phosphatase (as defined herein) in a suitable reaction medium, and determining the presence or extent of phosphorylation of dephosphorylation in the presence and absence of the candidate substance. A difference in activity in the presence and absence of the candidate substance is indicative of a modulating effect.

Preliminary assays in vitro may be followed by, or run in parallel with, in vivo assays.

Of course, the person skilled in the art will design any appropriate control experiments with which to compare results obtained in test assays.

Performance of an assay method according to the present invention may be followed by isolation and/or manufacture and/or use of a compound, substance or molecule which tests positive for ability to modulate interaction between one of the phosphorylation sites of tau protein (as defined herein) and a kinase (as disclosed herein) or a phosphatase.

The precise format of an assay of the invention may be varied by those of skill in the art using routine skill and knowledge. For example, interaction between substances may be studied in vitro by labelling one with a detectable label and bringing it into contact with the other which has been immobilised on a solid support. Suitable detectable labels, especially for peptidyl substances include $^{35}$S-methionine which may be incorporated into recombinantly produced peptides and polypeptides. Recombinantly produced peptides and polypeptides may also be expressed as a fusion protein containing an epitope which can be labeled with an antibody.

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above a test compound can be assayed by determining its ability to diminish the amount of labeled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

The amount of a candidate substance which may be added to an assay of the invention will normally be determined by trial and error depending upon the type of compound used. Typically, from about 0.001 nM to 1 mM or more concentrations of putative inhibitor compound may be used, for example from 0.01 nM to 100 μM, e.g. 0.1 to 50 μM, such as about 10 μM. Greater concentrations may be used when a peptide is the test substance. Even a molecule which has a weak effect may be a useful lead compound for further investigation and development.

Combinatorial library technology provides an efficient way of testing a potentially vast number of different substances for ability to modulate activity of a polypeptide. Such libraries and their use are known in the art. Compounds which may be used may be natural or synthetic chemical compounds used in drug screening programmes. Extracts of plants which contain several characterised or uncharacterised components may also be used.

Antibodies directed to the site of interaction in either protein form a further class of putative inhibitor compounds. Candidate inhibitor antibodies may be characterised and their binding regions determined to provide single chain antibodies and fragments thereof which are responsible for disrupting the interaction. Antibodies may also be employed as site specific recognition agents for determining whether phosphorylation of a site in tau protein has occurred during as assay.

Antibodies may be obtained using techniques which are standard in the art. Methods of producing antibodies include immunizing a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80-82). Isolation of antibodies and/or antibody-producing cells from an animal may be accompanied by a step of sacrificing the animal.

As an alternative or supplement to immunizing a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO 92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')$_2$ fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2 188 638 A or EP 0 239 400 A. Cloning and expression of chimeric antibodies are described in EP 0 120 694 A and EP 0 125 023 A.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. The mode of determining binding is not a feature of the present invention and those skilled in the art are able to choose a suitable mode according to their preference and general knowledge.

Other candidate inhibitor compounds may be based on modelling the 3-dimensional structure of a polypeptide or peptide fragment and using rational drug design to provide potential inhibitor compounds with particular molecular shape, size and charge characteristics.

Mass Spectroscopy

An LC/MS/MS based strategy was used to discover new phosphorylation sites within tau protein isolated from AD brain. So called PHF-tau was initially extracted from a heat-stable preparation of human AD brain material and subsequently further purified by ion exchange chromatography. Having been separated using SDS-PAGE, phospho-peptide mapping was then undertaken. Coomassie stained bands are excised, reduced, alkylated and enzymatically digested using a suite of proteases such as trypsin, chymotrypsin and endoproteinase Asp-N. Resulting peptide mixtures are then analysed by LC/MS/MS using a Q-TOF micro instrument with peptide separation achieved using a 75 micron ID Pep-Map reversed phase column with peptides eluted using a gradient of acetonitrile at a flowrate of 200 nl/min.

Database searching against bespoke index files is performed utilising the Mascot algorithm (Matrix Science). All MS/MS spectra relating to phosphopeptides are then subsequently visually verified to check the result.

Tandem MS/MS of peptides may be used to provide sequence information by virtue of the fragment ions produced. Fragmentation occurs generally across the peptide bond leading to a ladder of sequence ions that are diagnostic of the amino acid sequence. The difference between consecutive ions in a series indicates the mass of the amino acid at that position in the peptide. The most common ion types are b and y ions. The C-terminal containing fragments are designated y-ions and the N-terminal containing fragments are designated b-ions (Roepstorff, P., Fohlman, J. J. Biomed. Mass Spectrom. 1984, 11, 601). Peptides created by trypsin proteolysis and ionised by electrospray generally form ions that are doubly charged. This stems from the presence of basic groups within the peptide, namely, the alpha amino group at the N-terminus and the side chain of the C-terminal lysine or arginine. MS/MS spectra of such peptides generally yield a prominent y-type ion series in the high mass end of the spectrum (Bonner, R., Shushan, B. Rapid Commun. Mass Spectrom. 1995, 9, 1067-1076). Ideally, for de novo sequencing purposes, a complete set of complementary b and y ions will ensure a high confidence level for the proposed peptide sequence. Moreover, if fragment ions representing the complete sequence of the peptide are present, the site of attachment of the phosphate group can be deduced from the position and pattern of these fragment ions. Therefore, it is possible in most instances to discover the exact site of phosphorylation in each phosphopeptide. In some instances we have even found MS/MS spectra to be heterogeneous. Here two (or more) distinct phosphopeptides are represented in the same spectrum. This is because each phosphopeptide form has the same molecule weight and the same number of phosphate groups, but these are attached to different amino acids within the peptide. Therefore, both forms give rise to precursor ions of the same m/z ratio, which are then selected simultaneously by the mass spectrometer during the MS/MS experiment. In such cases, we refer to the phosphopeptides concerned as "regiomers"

Multiplex Assays for Screening Compounds

In drug development it is desirable to develop rapid high throughput assays with simple read out to show whether a compound has an effect on the proposed target. In the case of compounds inhibiting an enzyme function, such as a kinase, it is possible to develop an artificial substrate for the target enzyme that is modified by the enzyme in a way that the level of modification can be readily detected. In the presence of an inhibitory compound, the substrate is not modified and this can also be readily detected.

In the case of inhibitors of tau phosphorylation, it is necessary to monitor the effect of inhibiting specific protein kinases on the phosphorylation status of a large number of sites. In one aspect, it is possible to prepare artificial substrates corresponding to each of the phosphorylation sites on tau and assess each compound for their ability to inhibit the phosphorylation of each site independent of the other sites. In such a system, each compound would be added to multiple wells each well containing the proposed kinase target, one of the phosphorylation site-specific artificial substrates and a reporter system to show phosphorylation, such as a monoclonal antibody that binds specifically to the substrate in either the phosphorylated or unphosphorylated form, and which antibody is labeled with a fluorescent marker, an enzyme that converts a colour less substrate into a coloured product, or an enzyme that promotes the production of a luminescent signal. In such an assay, it is desirable that the artificial substrate for the target is immobilised on a solid surface such that as part of the assay procedure any unreacted antibody is removed from the system by washing before the result is read. Such assays may be run in microtitre wells of varying formats of typically 96, or more typically 384, or even more typically 1536 wells, or alternatively may be run on a microarray based on a solid support such as glass.

Alternatively, the effect of different kinase inhibitors on the global phosphorylation status of tau may be designed. In such an assay, full length recombinant tau protein carrying no phosphorylations, or one or more desirable phosphorylations may be used as the substrate. Alternatively, a mixture of equal amounts of all of the artificial substrates representing single phosphorylation sites may be used. Each screening assay will determine the effect of compounds on the inhibition of one, two or more protein kinases with known activity for the phosphorylation of tau. As with the more simple assays described above substrate, target kinase and compound are added to a well of a microtitre plate and incubated with appropriate buffers and other constituents that permit the phosphorylation of substrate in the absence of an inhibitory compound. The phosphorylation status of the substrate may then be determined using a mixture of antibodies or other molecules with specificity for individual phosphorylation sites on tau, wherein such antibodies or other molecules are each labeled with a unique reporter such as a fluorescent dye or compounds with unique spectral properties in infra-red, visible or ultraviolet spectra. After removal of antibodies that remain unbound to the phosphorylated substrate(s), levels of each specific reporter are determined using an appropriate reading device, and the levels of phosphorylation at each specific site in tau is revealed by comparison with a control where no kinase inhibitor was added.

In a preferred embodiment of such a multiplex screening assay, the substrate is dephosphorylated recombinant tau protein and the kinase is selected from CK1, CK2, GSK-3a, GSK-3b, PKA, CDK5, ERK1/2, SAPK1g, SAPK2a, SAPK2b, SAPK3, SAPK4, stress activated protein kinase family kinases (SAPKs) such as p38MAPK and JNK, MARK family kinases such as 110K, cdc2, cdk2, PKC, PKN, TTK, PKB, DYRK, PK, CaMKII, PKD, or a mixture of one of more these kinases. Reporter systems are preferably labeled antibodies, typically monoclonal antibodies, for example those that can be obtained from rabbits or mice using techniques well known in the art. Labels are preferably fluorescent or calorimetric compounds that are covalently attached to antibodies, more preferably fluorescent or calorimetric nanoparticles and are most preferably nanoparticles with unique Raman spectra.

Development of Mimetic Substances

Once candidate substance have been found in the assays and screens according to the present invention, they may be used to design mimetic compounds for development as drugs. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled according to its physical properties, e.g. stereochemistry, bonding, size and/or charge, using data from a range of sources, eg spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

Inhibitors

The term "inhibitor" is used in the broadest sense, and includes any molecule that partially or fully blocks, inhibits, or neutralizes the expression or kinase activity of a kinase. Preferably, a kinase inhibitor is a specific or near-specific inhibitor which inhibits the expression or activity a desired kinase without affecting other kinases.

Kinase inhibitors include antibodies, dominant negative forms and small molecule inhibitors.

Small molecule inhibitors of Abl activity include phenylaminopyrimidines such as imatinib or imatinib mesylate (Glivec/Gleevec™, 4-[)4-methyl-1-piperazinyl)methyl]-N-[4-methyl-3-[4-(3-pyridinyl)-2-pyrimidinyl[amino]-phenyl] benzamide methanesulfonate; Novartis); BMS-354825 [n-(2-chloro-6-methylphenyl)-2-(6-(4-(2-hydroxyethyl) piperazin-1-yl)-2-methylpyrimidin-4-ylamino)thiazole-5-carbozamide]; PD 173955 (Parke Davis); pyridopyrimidines such as PD166326 (Parke Davis); ON 012380 (Onconova).

Small molecule inhibitors of Syk activity include picetannol (3,4,3',5'-tetrahydroxy-trans-stilbene); 574711 (3-(1-Methyl-1H-indol-3-yl-methylene)-2-oxo-2,3-dihydro-1H-indole-5-sulfonamide, Calbiochem); ER-27319; and BAY61-3606.

Small molecule inhibitors of Fyn activity include PP1 (4-Amino-5-(4-methylphenyl)-7-(t-butyl)pyrazolo[3,4-d] pyrimidine).

Inhibitors of kinase expression include antisense RNA or siRNA as described below, triple-helix nucleic acids or ribozymes.

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra; Lee et al., *Nucl. Acids Res.,* 6:3073 (1979); Cooney et al., *Science,* 241: 456 (1988); Dervan et al., *Science,* 251:1360 (1991).

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469-471 (1994), and PCT publication No. WO 97/33551 (published Sep. 18, 1997).

Antisense

Expression of nucleic acid sequences that are complementary in sequence to a coding sequence of a gene ('antisense' nucleic acids) can inhibit production of the protein product from the gene. It is not known exactly how this occurs, but it is thought that the antisense nucleic acid sequences hybridise to cellular mRNA, forming a double stranded molecule. The cell does not translate the mRNA in this double-stranded form, so translation is inhibited. Antisense nucleic acids may have other effects, including inhibition of transcription and splicing inhibition.

The term 'antisense' nucleic acid indicates a nucleic acid sequence which is sufficiently complementary to the RNA molecule for which the antisense nucleic acid is specific to cause molecular hybridisation between the antisense nucleic acid and the mRNA such that translation of the mRNA is inhibited. Such hybridisation must occur under in vivo conditions, that is, inside the cell.

Oligomers of about fifteen nucleotides or greater and molecules that hybridise to the AUG initiation codon are particularly efficient, since they are easy to synthesize and are likely to pose fewer problems than larger molecules when introducing them into cells.

RNA Interference

RNA interference (RNAi) is a process of sequence-specific, post-transcriptional gene silencing in animals and plants, initiated by double-stranded RNA (dsRNA) that is homologous in sequence to the silenced gene. RNAi is mediated by short double-stranded RNA molecules (small interfering RNAs or siRNAs). siRNAs may be introduced into a cell as short RNA oligonucleotides of 10-15 bp, or as longer dsRNAs which are subsequently cleaved to produce siRNAs. The RNA may be introduced into the cell as RNA, or may be transcribed from a DNA or RNA vector.

Methods relating to the use of RNAi to silence genes in *C. elegans, Drosophila*, plants, and mammals are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619, and Elbashir S M, et al., 2001 Nature 411:494-498).

In some embodiments, the siRNA has an overhang at one or both ends of one or more deoxythymidine bases. The overhang is not to be interpreted as part of the siRNA sequence. Where present, it serves to increase the stability of the siRNA within cells by reducing its susceptibility to degradation by nucleases.

siRNA molecules may be synthesized using standard solid or solution phase synthesis techniques which are known in the art. Linkages between nucleotides may be phosphodiester bonds or alternatives, for example, linking groups of the formula P(O)S, (chioate); P(S)S, (dithioate); P(O)NR'2; P(O) R'; P(O)OR6; CO; or CONR'2 wherein R is H (or a salt) or alkyl (1-12C) and R6 is alkyl (1-9C) is joined to adjacent nucleotides through —O— or —S—.

Alternatively, siRNA molecules or longer dsRNA molecules may be made recombinantly by transcription of a nucleic acid sequence, preferably contained within a vector as described below.

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. The shRNA is then processed into an siRNA which degrades the target gene mRNA and suppresses expression. shRNAs can produced within a cell by transfecting the cell with a DNA construct encoding the shRNA sequence under control of a RNA polymerase III promoter, such as the human H1 or 7SK promoter.

Alternatively, the shRNA may be synthesised exogenously and introduced directly into the cell.

Preferably, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules which are more, or less, stable than unmodified siRNA.

The term 'modified nucleotide base' encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2'-azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5-methoxyuracil, 2-methylthio-N6-isopentenyladenine, uracil-5-oxyacetic acid methyl ester, psuedouracil, 2-thiocytosine, 5-methyl-2 thiouracil, 2-thiouracil, 4-thiouracil, 5-methyluracil, N-uracil-5-oxyacetic acid methylester, uracil 5-oxyacetic acid, queosine, 2-thiocytosine, 5-propyluracil, 5-propylcytosine, 5-ethyluracil, 5-ethylcytosine, 5-butyluracil, 5-pentyluracil, 5-pentylcytosine, and 2,6,diaminopurine, methylpsuedouracil, 1-methylguanine, 1-methylcytosine.

Pharmaceutical Compositions

Following identification of a substance which modulates or affects phosphorylation or dephosphorylation of tau protein, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified using the screening assays and assay methods disclosed herein, but also a pharmaceutical composition, medicament, drug or other composition comprising such a substance, a method comprising administration of such a composition to a patient, e.g. to treat tauopathies, use of such a substance in manufacture of a composition for administration for the treatment of tauopathies, and a method of making a pharmaceutical composition comprising admixing such a substance with a pharmaceutically acceptable excipient, vehicle or carrier, and optionally other ingredients.

The substances identified as kinase inhibitors or phosphatase promoters in the assays and assay methods of the present invention, or compounds or substances arising from further development or optimisation, may be formulated in pharmaceutical compositions. These compositions may be employed for the treatment of tauopathies, that is conditions which are characterised by neurofibrillary tangles or aggregates of tau protein. Tauopathies are a recognised class of conditions known to those skilled in the art and include Alzheimer's disease (AD), frontotemproal dementia with Parkinsonism linked to chromosome 17 (FTDP-17), progressive supranuclear palsy (PSP), Pick's disease, corticobasal degeneration and multiple system atrophy (MSA). The intracellular tau deposits are usually neuronal or glial and are filamentous and generally in a hyperphosphorylated state as compared to the level of phosphorylation in tau from control human brain. In the case of AD, this hyperphosphorylated tau is often referred to as paired helical filament tau (PHF) tau because it is derived from the PHF.

These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins. A composition may be administered alone or in combination with other treatments, either simultaneously or sequentially, dependent upon the condition to be treated.

EXPERIMENTAL

Purification of PHF-Tau from Alzheimer Brain

Paired helical filament (PHF) tau was purified from Alzheimer brain as described in Hanger et al, 1998. Briefly, brain tissue was homogenised and insoluble PHF-tau was recovered by differential centrifugation. Following solubilisation in guanidine and dialysis against a re-naturing buffer, PHF-tau was purified by anion-exchange and reversed-phase chromatography.

Preparation of Mutant Forms of Human Tau

To generate the five tau constructs each with a single tyrosine replaced by phenylalanine, a QuikChange® XL site-directed mutagenesis kit (Stratagene, Amsterdam, The Netherlands) was used. Primers (custom-synthesised by Sigma-Genosis) were as follows: to convert Tyr-18 to Phe (giving tau construct Y18F), forward primer 5'-CAC GCT GGG ACG TTC GGG TTG GGG GAC-3' (Primer A; SEQ ID NO: 5), and reverse primer 5'-GTC CCC CAA CCC GAA CGT CCC AGC GTG-3' (SEQ ID NO: 6); to convert Tyr-29 to Phe (giving Y29F), forward primer 5'-GAT CAG GGG GGC TTC ACC ATG CAC CAA G-3' (Primer B; SEQ ID NO: 7), and reverse primer 5'-C TTG GTG CAT GGT GAA GCC CCC CTG ATC-3' (SEQ ID NO: 8); to convert Tyr-197 to Phe (giving Y197F), 5'-GAT CGC AGC GGC TTC AGC AGC CCC GG-3' (Primer C; SEQ ID NO: 9), and reverse primer 5'-CC GGG GCT GCT GAA GCC GCT GCG ATC-3' (SEQ ID NO: 10); to convert Tyr-310 to Phe (giving Y310F), forward primer 5'-GGC AGT GTG CAA ATA GTC TTC AAA CCA GTT GAC CTG AG-3' (Primer D; SEQ ID NO: 11), and reverse primer 5'-CT CAG GTC AAC TGG TTT GAA GAC TAT TIG CAC ACT GCC-3' (SEQ ID NO: 12); and to convert Tyr-394 to Phe (giving Y394F), forward primer 5'-GCG GAG ATC GTG TTC AAG TCG CCA GTG G-3' (Primer E; SEQ ID NO: 13), and reverse primer 5'-C CAC TGG CGA CTT GAA CAC GAT CTC CGC-3' (SEQ ID NO: 14). The sequence of the full insert was determined for each construct (Lark Technologies).

To change all five tyrosines to phenylalanines a QuikChange® multi site-directed mutagenesis kit (Stratagene) was used, with the five primers A to E (above). Colonies were sequenced, and as well as identifying constructs where all five tyrosines had been replaced by phenylalanine (TauYallF), constructs with a single tyrosine remaining were found that contained four phenylalanines and just Tyr-18, Tyr-29 or Tyr-197. Mutants containing just Tyr-310 or just Tyr-394 were generated from the all-Phe construct by single site-directed mutagenesis as above using the following primers: for Tyr-310only, forward primer 5'-GGC AGT GTG CAA ATA GTC TAC AAA CCA GTT GAC CTG AG-3' (SEQ ID NO: 15), and reverse primer 5'-CT CAG GTC AAC TGG TTT GTA GAC TAT TTG CAC ACT GCC-3' (SEQ ID NO: 16); and for Tyr-394 only, forward primer 5'-GCG GAG ATC GTG TAC AAG TCG CCA GTG G-3' (SEQ ID NO: 17), and reverse primer 5'-C CAC TGG CGA CTT GTA CAC GAT CTC CGC-3' (SEQ ID NO: 18). The five constructs with one remaining tyrosine were termed Y18only, Y29only, etc, and their tau coding sequences verified (Lark Technologies).

Preparation and Purification of Recombinant Human Tau

A plasmid expressing the largest tau isoform (2N4R) was used to prepare and purify recombinant human tau as described previously (Mulot et al., 1994). Briefly, a bacterial cell lysate expressing 2N4R tau was heated and centrifuged to remove heat-labile proteins. The supernatant was fractionated with ammonium sulphate and precipitated material was solubilised and dialysed into buffer prior to cation-exchange chromatography. Proteins were eluted with NaCl and fractions containing tau were pooled and dialysed against Mes buffer pH 6.25, 5 mM DTT, and stored frozen.

In Vitro Phosphorylation of Recombinant Tau by Rat Brain Lysate

A rat brain extract containing active protein kinases was prepared by homogenising a rat brain in ice-cold buffer (2 ml buffer per g brain) containing 25 mM Tris-HCl pH 7.5, 5 mM EGTA, 2 mM dithiothreitol (DTT), 2 μM okadaic acid, 1 mM sodium orthovanadate and protease inhibitors. The homogenate was centrifuged at 100,000 g for 1 hr, and incubated on ice for 30 min with 2 mM ATP and 10 μM okadaic acid. This extract (rat brain supernatant, RBS) contained 7 mg/ml protein (Bradford).

Recombinant 2N4R tau protein (100 μg/ml) was phosphorylated by incubating with RBS (1.8 mg/ml protein) in 50 mM Tris-HCl buffer pH 7.5 with 5 mM $MgCl_2$, 3 mM ATP, 5 mM EGTA, 1 mM sodium orthovanadate, 10 μM okadaic acid, 1 mM DTT and protease inhibitors at 37° C. for 24 hr. The reaction mixture was then heated at 100° C. for 5 min, incubated on ice for 10 min, and centrifuged for 10 min at 16000 g. The supernatant containing the tau protein was aspirated off and analysed by Western blotting and mass spectrometry.

In Vitro Phosphorylation of Recombinant Tau by Tyrosine Protein Kinases

Recombinant human tau (1 μg) was incubated with 50 ng of either Abl or Syk (Upstate) in 30 μl of kinase buffer (HEPES 50 mM pH 7.4, 10 mM $MnCl_2$ in the presence of 1 mM ATP) for 30 minutes at 30° C. 30 μl of SDS-PAGE sample buffer was added to stop the reaction.

In Vitro Phosphorylation of Recombinant Tau by Lck and Subsequent Binding of SH2 Domain of Fyn Recombinant 2N4R tau protein (440 μg/ml) was incubated at 30° with purified recombinant Lck (20-100 μg/ml), 40 mM β-glycerophosphate buffer pH 7.5, 3 mM ATP, 25 mM $MgCl_2$, 5 mM $MnCl_2$, 1 mM DTT, 100 μM EDTA, 1 mM sodium orthovanadate and protease inhibitors. After 6 hr the tubes were heated at 100° for 5 min, cooled for 10 min on ice, and centrifuged for 10 min at 16000 g. The supernatants were checked for tyrosine phosphorylation by Western blotting, using 4G10 anti-phosphotyrosine antibody (Upstate, Inc) and anti-tau antibody (Dako).

Interaction of tau with the SH2 domain of Fyn was investigated by incubating tyrosine-phosphorylated or non-phosphorylated tau (5pg/ml) with glutathione-Sepharose® beads containing 2-5pg of GST-Fyn-SH2 fusion protein or GST as control. After mixing for 60 min at 4° the beads were washed ×3 and analysed by Western blotting for tau and for phosphotyrosine as above.

In-Gel Proteolytic Digestion of Tau

PHF-tau or in vitro phosphorylated tau proteins were separated on 10% (wt/vol) polyacrylamide gels and stained with colloidal Coomassie Blue G. Protein bands corresponding to tau were excised, carbamidomethylated, and digested with proteolytic enzymes (trypsin or Asp-N). Peptides were extracted from gel pieces by a series of acetonitrile and aqueous washes, dried and resuspended in 50 mM ammonium bicarbonate.

Amyloid Beta Treatment of Neurons and Isolation of Lipid Rafts

Rat and human primary cortical neuronal cultures were treated with fibrillar $A\beta_{25-35}$ or $A\beta_{1-42}$ for 1-30 min. Lipid rafts were prepared from control untreated and Aβ-treated neuronal cultures by scraping the cells from one 80 $cm^2$ flask into 2 ml 1% Triton X-100 in 25 mM Mes, pH 6.5 containing protease inhibitors. Cells were disrupted by Dounce homgenization. The homogenate was mixed with 2 ml of 90% sucrose (w/v) in 25 mM Mes, 150 mM NaCl pH 6.5 and placed in a 12 ml centrifuge tube. A 5-35% step sucrose gradient was formed by overlaying the homogenate mix with 4 ml of a 35% (w/v) sucrose solution followed by 4 ml of a 5% (w/v) sucrose solution. This was then centrifuged at 39,000 rpm for 18 hr in a Beckman SW41 rotor. 1 ml fractions were collected from the top of each gradient. The lipid raft fraction partitioned at the interface between the 5% (w/v) sucrose layer and the 35% sucrose (w/v) layer, fractions 4 and 5. Lipid raft fractions were concentrated by mixing the raft fractions (4 and 5) with 10 ml dd $H_2O$ and centrifuging at 39,000 rpm for 2 h in a Beckman SW41 rotor. The supernatant was aspirated and the remaining pellet was resuspended in 100 μl of 2× sample buffer. Western blots of lipid raft proteins were probed for antibodies to flotillin and protein loading corrected by scanning densitometry. Tau was detected in lipid rafts by probing western blots of lipid raft proteins using a polyclonal anti-tau antibody (DAKO).

Phosphorylation of Tyrosine Residues in Tau in Cultured Cells Treated with Pervanadate In a first set of experiments, COS-7 cells were transiently transfected with V5 tagged human tau longest isoform or with V5 tagged mutants of tau where one tyrosine has been replaced by one phenylalanine (named Y18F, Y29F, Y197F, Y310F and Y394F) constructs. In a second set of experiments, COS-7 cells were transiently transfected with the V5 tagged tau (441) construct or with V5 tagged mutants of tau where only one tyrosine is remaining, the four other tyrosines being replaced by phenylalanine (named Y18-only, Y29-only, Y197-only, Y310-only and Y394-only according to the remaining tyrosine). In order to increase tau tyrosine phosphorylation, cells were treated with the tyrosine phosphatase inhibitor pervanadate for 20 minutes. Cells were harvested in NETF buffer (100 mM NaCl, 2 mM EGTA, 50 mM Tris-Cl pH 7,4 and 50 mM NaF) containing 1% NP-40, 2 mM orthovanadate and protease inhibitors. Samples were precleared with 40 μl of protein G-Sepharose beads, and immunoprecipitations were carried out with monoclonal anti-V5 antibodies preadsorbed on protein G-Sepharose beads. Cells were harvested in NETF lysis buffer containing 1% NP-40 and tau was immunoprecipitated using an anti-V5 antibody. Resulting immunoprecipitates were separated in duplicate by SDS-PAGE and transferred to nitrocellulose. Immunoblots were performed cn duplicate membranes using 4G10 phosphotyrosine antibody or TP70 antibody (total tau antibody). Bound antibodies were visualized by enhanced chemiluminescence detection. Quantification was achieved by scanning the autoradiograms with GS710 Calibrated Imaging Densitometer (Bio-Rad) and measurement of relative optical density with Quantity One 4.0.3 software (Bio-Rad).

Phosphorylation of Tyrosine Residues in tau in Cultured Cells by Co-Expression of Tyrosine Kinases, Fyn, Src, Abl, Syk Fyn cDNA was a gift from D. Markby (Sugen, San Francisco), Src cDNA was from upstate (Src cDNA allelic pack), Abl and AblΔXB cDNA (a constitutively active form of Abl, with deletion of most of the SH3 domain) were from Richard A. Van Etten (Molecular Oncology Research Institute, Boston), Syk cDNA was a gift from H. Band (Brigham and Women's Hospital, Boston). CHO cells were used for the co-transfection experiments. CHO cells were transiently transfected with the V5 tagged human tau longest isoform and with V5 tagged mutants of tau where one tyrosine has been replaced by one phenylalanine (named Y18F, Y29F, Y197F, Y310F and Y394F) constructs. In every experiment, cells were co-transfected with the empty vector or with the protein tyrosine kinase expression vector (Fyn, Src, Abl or AblΔXB). Harvesting of cells, immunoprecipitation and Western analysis were performed as described in the section "Phosphorylation of tyrosine residues in tau in cultured cells treated with pervanadate".

Results

New Sites of Tyrosine Phosphorylation Found in PHF-Tau

Current literature reports 25 known phosphorylation sites (all are serine or threonine) identified by direct means in PHF-tau (Hanger et al, 1998) (Morishima-Kawashima et al., 1995). There are a further 2-3 sites that have been identified by antibody reactivity only. On the basis of antibody labelling, it has been reported that tyrosine 18 is phosphorylated in a proportion of PHF-tau in AD brain. We have found an additional 12 phosphorylation sites in PHF-tau, one of which is a tyrosine residue (tyr394), bringing the total number of sites to 37. We have also found that tyr394 is phosphorylated in tau isolated from human foetal brain.

New Sites of Tyrosine Phosphorylation on Recombinant Tau Generated by Rat Brain Lysate Mass spectrometry of proteolytic digests of tau that had been phosphorylated with rat brain supernatant demonstrated phosphorylation on tyrosines 310 and 394, in addition to many serines and threonines.

Aβ treatment of neurons and lipid raft composition $A\beta_{25-35}$ and $A\beta_{1-42}$ treatment of primary rat neuronal cultures resulted in a rapid increase in the tyrosine phosphorylation of neuronal protein components of lipid rafts. No increase in the phosphoserine or phosphothreonine content of lipid raft proteins was observed after Aβ-treatment. The increase in tyrosine phosphorylation was concomitant with an increased partitioning of Fyn, tau, and tubulin into lipid rafts. Focal adhesion kinase (FAK) levels transiently increased in lipid rafts in response to Aβ while levels of the classic lipid raft protein flotillin remained unchanged. Inhibition of tyrosine phosphorylation with the tyrosine kinase inhibitor PP2 abrogated the Aβ-induced increase in tyrosine phosphorylation of lipid raft proteins and partitioning of tau into lipid rafts.

Phosphorylation of Tyrosine Residues in Tau in Cultured Cells Treated with Pervanadate The first set of five mutants where one tyrosine residue was exchanged with phenylalanine (Y18F, Y29F, Y197F, Y310F and Y394F) were transfected into COS-7 cells and cells were treated for 20 minutes with pervanadate. Western analysis performed on immunoprecipitated tau, using 4G10 antiphosphotyrosine antibody shows that the Y394F mutant construct is the only single tyrosine mutation that results in a significant effect, reducing tyrosine phosphorylation to approximately 10% of the wild-type control. Tyrosine phosphorylation of the Y18F, Y29F, Y310F constructs were not significantly different from the wild-type control. Concerning the Y197F mutant construct, it should be pointed out that a decrease in tyrosine phosphorylation was observed in two of the five experiments that were done with this construct. To confirm these results, we transfected into COS-7 cells the second set of mutants in which only one tyrosine residue remains as the sole tyrosine with the other four replaced by phenylalanine (Y18-only, Y29-only, Y197-only, Y310-only and Y394-only). Analysis using phosphotyrosine antibodies showed that no tyrosine phosphorylation could be elicited by pervanadate in Y18-only, Y29-only, Y310-only mutant constructs, whereas pervanadate induces an increase in tyrosine phosphorylation of the Y394-only similar to the one observed in wild-type tau. In two of the four experiments made with the Y197-only mutant construct, a faint but clear-cut phosphotyrosine immunoreactivity was detectable. Taken together, these results suggest that the majority of tyrosine phosphorylation of tau in pervanadate-treated COS-7 cells occurs on tyrosine 394.

Phosphorylation of Tyrosine Residues in Tau in Cultured Cells Over Expressing Fyn Wild type tau and the first set of five mutants where one tyrosine residue was exchanged with phenylalanine (Y18F, Y29F, Y197F, Y310F and Y394F) were co-transfected with the empty vector or with a Fyn-expression vector into CHO cells. Western analysis performed on immunoprecipitated tau, using 4G10 phosphotyrosine antibody, shows that the Y18F and Y310F mutant constructs are the two single tyrosine mutations that results in a significant effect, each mutation reducing tyrosine phosphorylation to approximately 50% of the wild-type control. Taken together, the results suggest that tyrosine 18 and 310 are the main sites phosphorylated by Fyn.

Phosphorylation of Tyrosine Residues in Tau in Cultured Cells Over-Expressing Abl Wild type tau and the first set of five mutants where one tyrosine residue was exchanged with phenylalanine (Y18F, Y29F, Y197F, Y310F and Y394F) were co-transfected with the empty vector or with AblΔXB expression vector into CHO cells. Western analysis performed on immunoprecipitated tau, using 4G10 phosphotyrosine antibodies, shows that the Y394F is the tyrosine mutation with the strongest effect reducing tyrosine phosphorylation to approximately 25% of the wild-type control. Y197F and Y310F mutant constructs also have a significant effect reducing tyrosine phosphorylation to approximately 70% of the wild-type control each. In contrast, Y18F and Y29F mutant constructs were not different from the wild type control. Taken together, the results suggest that Abl primarily phosphorylates tau on tyrosine 394 and that tyrosines 197 and 310 are also phosphorylated by this kinase. In contrast, Abl does not phosphorylate tyrosines 18 and 29.

Phosphorylation of Tyrosine Residues in Tau in Cultured Neurons Over-Expressing Syk Wild type tau and the first set of five mutants where one tyrosine residue was exchanged with phenylalanine (Y18F, Y29F, Y197F, Y310F and Y394F) were co-transfected with the empty vector or with a Syk expression vector into CHO cells. Western analysis performed on immunoprecipitated tau, using 4G10 phosphotyrosine antibodies, shows that single mutants of tau (i.e. with one tyrosine mutated to phenylalanine, the other four tyrosines still being present) showed no significant decreases in tau tyrosine phosphorylation. Mutants with only Y18, Y29, Y197 or Y394 could each be phosphorylated to 20-25% of the level found with wild-type, indicating that Syk can phosphorylate tau at each of these sites.

SH2 Domain of Fyn Binding to Tyrosine-Phosphorylated Tau

Co-sedimentation experiments using GST-SH2 proteins bound to glutathione beads demonstrated that tyrosine phosphorylated tau, but not control non-phosphorylated tau, could bind to the SH2 domain of Fyn (isoform B).

Use of STI 571 to Determine Whether Phosphorylation of Tau in Cells is Catalysed by an Abl-Like Kinase The chemical compound STI 571, also known as Imatinib mesylate, Gleevec®, Glivec, formerly CGP 57148B, chemical name 4-[(4-Methyl-1-piperazinyl)methyl]-N-[4-methyl-3-[[4-(3-pyridinyl)-2-pyrimidinyl]amino]-phenyl]benzamide methanesulphonate, is a known inhibitor of tyrosine protein kinases and an effective antileukaemic agent. It is selective for Abl but also inhibits a small number of other tyrosine protein kinases including the platelet-derived growth factor receptor and c-Kit.

An experiment to confirm whether an Abl-like kinase phosphorylates tau in cells could be carried out as follows. COS-7, CHO or SH-SY5Y cells are transfected with a suitable tau construct, e.g. a plasmid containing Tau2N4R-V5-His (wild-type) and after 48 hours treated with STI-571 followed 1 hour later with 100 micromolar pervanadate or control.

After a further one hour cells are harvested and cell lysates are immunoprecipitated with anti-V5 antibody and analysed by Western blotting with the antiphosphotyrosine antibody 4G10. It would be expected that, as already shown with the compound PP2, STI 571 will inhibit the tyrosine-phosphorylation of tau.

Hypothesis

Our hypothesis is that Aβ is neurotoxic to neurons by a mechanism that obligatorily requires the involvement of tau and certain protein tyrosine kinases; likely candidate tyrosine kinases include Fyn and Abl but others may be required. We envisage a mechanism in which exposure of neurons to Aβ induces activation of one or more of these tyrosine kinases, which then phosphorylate tau and this generates binding sites for other cell signalling proteins, including for example an SH2 binding site for Fyn. Tyrosine phosphorylated tau then binds to lipid raft components of cell membranes in amounts that are pathological and this triggers unknown but detrimental cell signalling processes that result in neurodegeneration and cell death.

References

The references cited herein are all expressly incorporated by reference.

Dunah, A. W., Sirianni, A. C., Fienberg, A. A., Bastia, E., Schwarzschild, M. A., and Standaert, D. G. (2004). Dopamine D1-dependent trafficking of striatal N-methyl-D-aspartate glutamate receptors requires Fyn protein tyrosine kinase but not DARPP-32. Mol. Pharmacol. 65, 121-129.

Eckert, G. P., Cairns, N. J., Maras, A., Gattaz, W. F., and Müller, W. E. (2000). Cholesterol modulates the membrane-disordering effects of beta-amyloid peptides in the hippocampus: Specific changes in Alzheimer's disease. Dementia 11, 181-186.

Girardot, N., Allinquant, B., Langui, D., Laquerriere, A., Dubois, B., Hauw, J. J., and Duyckaerts, C. (2003). Accumulation of flotillin-1 in tangle-bearing neurones of Alzheimer's disease. Neuropathol. Appl. Neurobiol. 29, 451-461.

Hanger, D. P., Betts, J. C., Loviny, T. L., Blackstock, W. P., and Anderton, B. H. (1998). New phosphorylation sites identified in hyperphosphorylated tau (paired helical filament-tau) from Alzheimer's disease brain using nanoelectrospray mass spectrometry. J. Neurochem. 71, 2465-2476.

Lambert, M. P., Barlow, A. K., Chromy, B. A., Edwards, C., Freed, R., Liosatos, M., Morgan, T. E., Rozovsky, I., Trommer, B., Viola, K. L., Wals, P., Zhang, C., Finch, C. E., Krafft, G. A., and Klein, W. L. (1998). Diffusible, non-fibrillar ligands derived from Aβ$_{1-42}$ are potent central nervous system neurotoxins. Proc. Natl. Acad. Sci. USA 95, 6448-6453.

Ledesma, M. D., Abad-Rodriguez, J., Galvan, C., Biondi, E., Navarro, P., Delacourte, A., Dingwall, C., and Dotti, C. G. (2003). Raft disorganization leads to reduced plasmin activity in Alzheimer's disease brains. EMBO Rep. 4, 1190-1196.

Lee, G., Newman, S. T., Gard, D. L., Band, H., and Panchamoorthy, G. (1998). Tau interacts with src-family non-receptor tyrosine kinases. J. Cell Sci. 111, 3167-3177.

Lee, G., Thangavel, R., Sharma, V. M., Litersky, J. M., Bhaskar, K., Fang, S. M., Do, L. H., Andreadis, A., Van Hoesen, G., and Ksiezak-Reding, H. (2004). Phosphorylation of tau by fyn: implications for Alzheimer's disease. J. Neurosci. 24, 2304-2312.

Lee, V. M. Y., Goedert, M., and Trojanowski, J. Q. (2001). Neurodegenerative tauopathies. Annu. Rev. Neurosci. 24, 1121-1159.

Li, S. H., Yu, Z. X., Li, C. L., Nguyen, H. P., Zhou, Y. X., Deng, C., and Li, X. J. (2003). Lack of huntingtin-associated protein-1 causes neuronal death resembling hypothalamic degeneration in Huntington's disease. J. Neurosci. 23, 6956-6964.

Liu, T., Perry, G., Chan, H. W., Verdile, G., Martins, R. N., Smith, M. A., and Atwood, C. S. (2004). Amyloid-beta-induced toxicity of primary neurons is dependent upon differentiation-associated increases in tau and cyclin-dependent kinase 5 expression. J. Neurochem. 88, 554-563.

McDonald, D. R., Brunden, K. R., and Landreth, G. E. (1997). Amyloid fibrils activate tyrosine kinase-dependent signaling and superoxide production in microglia. J. Neurosci. 17, 2284-2294.

Morishima-Kawashima, M., Hasegawa, M., Takio, K., Suzuki, M., Yoshida, H., Titani, K., and Ihara, Y. (1995). Proline-directed and non-proline-directed phosphorylation of PHF-tau. J. Biol. Chem. 270, 823-829.

Mulot, S. F. C., Hughes, K., Woodgett, J. R., Anderton, B. H., and Hanger, D. P. (1994). PHF-tau from Alzheimer's brain comprises four species on SDS-PAGE which can be mimicked by in vitro phosphorylation of human brain tau by glycogen synthase kinase-3b. FEBS Lett. 349, 359-364.

Negro, A., Brunati, A. M., Donella-Deana, A., Massimino, M. L., and Pinna, L. A. (2002). Multiple phosphorylation of alpha-synuclein by protein tyrosine kinase Syk prevents eosin-induced aggregation. FASEB J. 16, 210-212.

Rapoport, M., Dawson, H. N., Binder, L. I., Vitek, M. P., and Ferreira, A. (2002). Tau is essential to beta-amyloid-induced neurotoxicity. Proc. Natl. Acad. Sci. U.S. A 99, 6364-6369.

Scales, T. M. E., Williamson, R., Anderton, B. H., and Reynolds, C. H. Tyrosine phosphorylation of specific sites on tau by Src family kinases. Neurobiology of Aging 23, S500-S501. 2002.
Ref Type: Generic Shirazi, S. K. and Wood, J. G. (1993). The protein tyrosine kinase, fyn, in Alzheimer's disease pathology. Neuroreport 4, 435-437.

Subasinghe, S., Unabia, S., Barrow, C. J., Mok, S. S., Aguilar, M. I., and Small, D. H. (2003). Cholesterol is necessary both for the toxic effect of Abeta peptides on vascular smooth muscle cells and for Abeta binding to vascular smooth muscle cell membranes. J. Neurochem. 84, 471-479.

Wang, S. S., Rymer, D. L., and Good, T. A. (2001). Reduction in cholesterol and sialic acid content protects cells from the toxic effects of beta-amyloid peptides. J. Biol. Chem. 276, 42027-42034.

Williamson, R., Scales, T., Clark, B. R., Gibb, G., Reynolds, C. H., Kellie, S., Bird, I. N., Varndell, I. M., Sheppard, P. W., Everall, I., and Anderton, B. H. (2002). Rapid tyrosine phosphorylation of neuronal proteins including tau and focal adhesion kinase in response to amyloid-b peptide exposure: involvement of Src family protein kinases. J. Neurosci. 22, 10-20.

Yip, C. M., Elton, E. A., Darabie, A. A., Morrison, M. R., and McLaurin, J. (2001). Cholesterol, a modulator of membrane-associated Ab-fibrillogenesis and neurotoxicity. J. Mol. Biol. 311, 723-734.

Zukerberg, L. R., Patrick, G. N., Nikolic, M., Humbert, S., Wu, C. L., Lanier, L. M., Gertler, F. B., Vidal, M., Van Etten, R. A., and Tsai, L. H. (2000). Cables links Cdk5 and c-Abl and facilitates Cdk5 tyrosine phosphorylation, kinase upregulation, and neurite outgrowth. Neuron 26, 633-646.

The invention claimed is:

1. An in vitro method of screening for substances which are candidate therapeutic agents for the treatment of a tauopathy selected from the group consisting of Alzheimer's disease (AD), frontotemproal dementia with Parkinsonism linked to chromosome 17 (FTDP-17), progressive supranuclear palsy (PSP), Pick's disease, corticobasal degeneration and multiple system atrophy (MSA), said substance being effective to inhibit the phosphorylation of a tau protein by a tyrosine kinase, wherein the tau protein comprises at least one phosphorylation site, the method comprising:

(a) contacting at least one said substance, the tau protein and the tyrosine kinase under conditions in which the tyrosine kinase is capable of phorphorylating said phosphorylation site(s) of the tau protein in the absence of the substance;

(b) detecting whether, and optionally the extent to which, said substance inhibits the phosphorylation of the tau protein at said at least one phosphorylation site of the tau protein by the tyrosine kinase; and, (c) selecting the substance which inhibits phosphorylation of the tau protein at said at least one site;

wherein the tyrosine kinase is c-Abl;

and wherein the tau protein is a protein which undergoes phosphorylation by c-Abl and has at least 80% sequence identity with the amino acid sequence of SEQ ID NO: 1, or a fragment of said tau protein, said fragment comprising at least 25 amino acids and including at least one said phosphorylation site.

2. The method of claim 1, wherein the tau protein is in the form of a paired helical filament tau.

3. The method of claim 1, wherein the tau protein has at least 90% sequence identity with the tau protein having the amino acid sequence set out in SEQ ID NO: 1.

4. The method of claim 1, wherein c-Abl phosphorylates the tau protein at one or more sites selected from the group consisting of Y197, Y310 and Y394 of the tau protein.

5. The method of claim 4, wherein c-Abl phosphorylates tau protein at Y394 of tau protein.

6. The method of claim 1, wherein the step of determining the presence, absence or extent of phosphorylation at one or more sites of the tau protein employs mass spectroscopy or a site specific recognition agent which is capable of distinguishing between phosphorylated and-non-phosphorylated sites.

* * * * *

UNITED STATES PATENT AND TRADEMARK OFFICE
CERTIFICATE OF CORRECTION

PATENT NO. : 8,367,360 B2 Page 1 of 1
APPLICATION NO. : 11/630720
DATED : February 5, 2013
INVENTOR(S) : Ward et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1158 days.

Signed and Sealed this
First Day of September, 2015

Michelle K. Lee
*Director of the United States Patent and Trademark Office*

```
                         SEQUENCE LISTING

<160> NUMBER OF SEQ ID NOS: 18

<210> SEQ ID NO 1
<211> LENGTH: 441
<212> TYPE: PRT
<213> ORGANISM: Homo sapiens

<400> SEQUENCE: 1

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335
```

```
Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Asn
            355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
            435                 440

<210> SEQ ID NO 2
<211> LENGTH: 1130
<212> TYPE: PRT
<213> ORGANISM: Homo sapiens

<400> SEQUENCE: 2

Met Leu Glu Ile Cys Leu Lys Leu Val Gly Cys Lys Ser Lys Lys Gly
1               5                   10                  15

Leu Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
        35                  40                  45

Asn Ser Lys Glu Asn Leu Leu Ala Gly Pro Ser Glu Asn Asp Pro Asn
50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
        115                 120                 125

His Gly Pro Val Ser Arg Asn Ala Ala Glu Tyr Leu Leu Ser Ser Gly
            130                 135                 140

Ile Asn Gly Ser Phe Leu Val Arg Glu Ser Glu Ser Ser Pro Gly Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His Ser Thr Val Ala Asp Gly
        195                 200                 205

Leu Ile Thr Thr Leu His Tyr Pro Ala Pro Lys Arg Asn Lys Pro Thr
210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gly Gln Tyr Gly Glu Val
                245                 250                 255

Tyr Glu Gly Val Trp Lys Lys Tyr Ser Leu Thr Val Ala Val Lys Thr
            260                 265                 270
```

```
Leu Lys Glu Asp Thr Met Glu Val Glu Glu Phe Leu Lys Glu Ala Ala
        275                 280                 285

Val Met Lys Glu Ile Lys His Pro Asn Leu Val Gln Leu Leu Gly Val
        290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
                340                 345                 350

Tyr Leu Glu Lys Lys Asn Phe Ile His Arg Asp Leu Ala Ala Arg Asn
        355                 360                 365

Cys Leu Val Gly Glu Asn His Leu Val Lys Val Ala Asp Phe Gly Leu
370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
                405                 410                 415

Ser Ile Lys Ser Asp Val Trp Ala Phe Gly Val Leu Leu Trp Glu Ile
                420                 425                 430

Ala Thr Tyr Gly Met Ser Pro Tyr Pro Gly Ile Asp Leu Ser Gln Val
                435                 440                 445

Tyr Glu Leu Leu Glu Lys Asp Tyr Arg Met Glu Arg Pro Glu Gly Cys
        450                 455                 460

Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
                485                 490                 495

Phe Gln Glu Ser Ser Ile Ser Asp Glu Val Glu Lys Glu Leu Gly Lys
                500                 505                 510

Gln Gly Val Arg Gly Ala Val Ser Thr Leu Leu Gln Ala Pro Glu Leu
        515                 520                 525

Pro Thr Lys Thr Arg Thr Ser Arg Arg Ala Ala Glu His Arg Asp Thr
        530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Gly Leu Asn Glu Asp Glu Arg Leu Leu Pro
                580                 585                 590

Lys Asp Lys Lys Thr Asn Leu Phe Ser Ala Leu Ile Lys Lys Lys Lys
        595                 600                 605

Lys Thr Ala Pro Thr Pro Pro Lys Arg Ser Ser Ser Phe Arg Glu Met
        610                 615                 620

Asp Gly Gln Pro Glu Arg Arg Gly Ala Gly Glu Glu Glu Gly Arg Asp
625                 630                 635                 640

Ile Ser Asn Gly Ala Leu Ala Phe Thr Pro Leu Asp Thr Ala Asp Pro
                645                 650                 655

Ala Lys Ser Pro Lys Pro Ser Asn Gly Ala Gly Val Pro Asn Gly Ala
                660                 665                 670

Leu Arg Glu Ser Gly Gly Ser Gly Phe Arg Ser Pro His Leu Trp Lys
        675                 680                 685

Lys Ser Ser Thr Leu Thr Ser Ser Arg Leu Ala Thr Gly Glu Glu Glu
        690                 695                 700
```

```
Gly Gly Gly Ser Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
            725                 730                 735

Pro Arg Asp Leu Gln Ser Thr Gly Arg Gln Phe Asp Ser Ser Thr Phe
            740                 745                 750

Gly Gly His Lys Ser Glu Lys Pro Ala Leu Pro Arg Lys Arg Ala Gly
            755                 760                 765

Glu Asn Arg Ser Asp Gln Val Thr Arg Gly Thr Val Thr Pro Pro Pro
770                 775                 780

Arg Leu Val Lys Lys Asn Glu Ala Ala Asp Glu Val Phe Lys Asp
785                 790                 795                 800

Ile Met Glu Ser Ser Pro Gly Ser Ser Pro Asn Leu Thr Pro Lys
            805                 810                 815

Pro Leu Arg Arg Gln Val Thr Val Ala Pro Ala Ser Gly Leu Pro His
            820                 825                 830

Lys Glu Glu Ala Glu Lys Gly Ser Ala Leu Gly Thr Pro Ala Ala Ala
            835                 840                 845

Glu Pro Val Thr Pro Thr Ser Lys Ala Gly Ser Gly Ala Pro Gly Gly
            850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
            885                 890                 895

Pro Ala Pro Pro Pro Pro Ala Ala Ser Ala Gly Lys Ala Gly Gly
            900                 905                 910

Lys Pro Ser Gln Ser Pro Ser Gln Glu Ala Ala Gly Glu Ala Val Leu
            915                 920                 925

Gly Ala Lys Thr Lys Ala Thr Ser Leu Val Asp Ala Val Asn Ser Asp
930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
            965                 970                 975

Ser Pro Ala Pro Val Pro Ser Thr Leu Pro Ser Ala Ser Ser Ala Leu
            980                 985                 990

Ala Gly Asp Gln Pro Ser Ser Thr Ala Phe Ile Pro Leu Ile Ser Thr
            995                 1000                1005

Arg Val Ser Leu Arg Lys Thr Arg Gln Pro Pro Glu Arg Ile Ala Ser
    1010                1015                1020

Gly Ala Ile Thr Lys Gly Val Val Leu Asp Ser Thr Glu Ala Leu Cys
1025                1030                1035                1040

Leu Ala Ile Ser Arg Asn Ser Glu Gln Met Ala Ser His Ser Ala Val
                1045                1050                1055

Leu Glu Ala Gly Lys Asn Leu Tyr Thr Phe Cys Val Ser Tyr Val Asp
                1060                1065                1070

Ser Ile Gln Gln Met Arg Asn Lys Phe Ala Phe Arg Glu Ala Ile Asn
                1075                1080                1085

Lys Leu Glu Asn Asn Leu Arg Glu Leu Gln Ile Cys Pro Ala Thr Ala
                1090                1095                1100

Gly Ser Gly Pro Ala Ala Thr Gln Asp Phe Ser Lys Leu Leu Ser Ser
1105                1110                1115                1120

Val Lys Glu Ile Ser Asp Ile Val Gln Arg
```

<210> SEQ ID NO 3
<211> LENGTH: 635
<212> TYPE: PRT
<213> ORGANISM: Homo sapiens

<400> SEQUENCE: 3

```
Met Ala Ser Ser Gly Met Ala Asp Ser Ala Asn His Leu Pro Phe Phe
 1               5                  10                  15

Phe Gly Asn Ile Thr Arg Glu Glu Ala Glu Asp Tyr Leu Val Gln Gly
            20                  25                  30

Gly Met Ser Asp Gly Leu Tyr Leu Leu Arg Gln Ser Arg Asn Tyr Leu
        35                  40                  45

Gly Gly Phe Ala Leu Ser Val Ala His Gly Arg Lys Ala His His Tyr
    50                  55                  60

Thr Ile Glu Arg Glu Leu Asn Gly Thr Tyr Ala Ile Ala Gly Gly Arg
65                  70                  75                  80

Thr His Ala Ser Pro Ala Asp Leu Cys His Tyr His Ser Gln Glu Ser
                85                  90                  95

Asp Gly Leu Val Cys Leu Leu Lys Lys Pro Phe Asn Arg Pro Gln Gly
            100                 105                 110

Val Gln Pro Lys Thr Gly Pro Phe Glu Asp Leu Lys Glu Asn Leu Ile
        115                 120                 125

Arg Glu Tyr Val Lys Gln Thr Trp Asn Leu Gln Gly Gln Ala Leu Glu
    130                 135                 140

Gln Ala Ile Ile Ser Gln Lys Pro Gln Leu Glu Lys Leu Ile Ala Thr
145                 150                 155                 160

Thr Ala His Glu Lys Met Pro Trp Phe His Gly Lys Ile Ser Arg Glu
                165                 170                 175

Glu Ser Glu Gln Ile Val Leu Ile Gly Ser Lys Thr Asn Gly Lys Phe
            180                 185                 190

Leu Ile Arg Ala Arg Asp Asn Asn Gly Ser Tyr Ala Leu Cys Leu Leu
        195                 200                 205

His Glu Gly Lys Val Leu His Tyr Arg Ile Asp Lys Asp Lys Thr Gly
    210                 215                 220

Lys Leu Ser Ile Pro Glu Gly Lys Lys Phe Asp Thr Leu Trp Gln Leu
225                 230                 235                 240

Val Glu His Tyr Ser Tyr Lys Ala Asp Gly Leu Leu Arg Val Leu Thr
                245                 250                 255

Val Pro Cys Gln Lys Ile Gly Thr Gln Gly Asn Val Asn Phe Gly Gly
            260                 265                 270

Arg Pro Gln Leu Pro Gly Ser His Pro Ala Thr Trp Ser Ala Gly Gly
        275                 280                 285

Ile Ile Ser Arg Ile Lys Ser Tyr Ser Phe Pro Lys Pro Gly His Arg
    290                 295                 300

Lys Ser Ser Pro Ala Gln Gly Asn Arg Gln Glu Ser Thr Val Ser Phe
305                 310                 315                 320

Asn Pro Tyr Glu Pro Glu Leu Ala Pro Trp Ala Ala Asp Lys Gly Pro
                325                 330                 335

Gln Arg Glu Ala Leu Pro Met Asp Thr Glu Val Tyr Glu Ser Pro Tyr
            340                 345                 350

Ala Asp Pro Glu Glu Ile Arg Pro Lys Glu Val Tyr Leu Asp Arg Lys
        355                 360                 365

Leu Leu Thr Leu Glu Asp Lys Glu Leu Gly Ser Gly Asn Phe Gly Thr
```

```
                370             375             380
Val Lys Lys Gly Tyr Tyr Gln Met Lys Val Lys Thr Val Ala
385                 390                 395                 400

Val Lys Ile Leu Lys Asn Glu Ala Asn Asp Pro Ala Leu Lys Asp Glu
                    405                 410                 415

Leu Leu Ala Glu Ala Asn Val Met Gln Gln Leu Asp Asn Pro Tyr Ile
                420                 425                 430

Val Arg Met Ile Gly Ile Cys Glu Ala Glu Ser Trp Met Leu Val Met
            435                 440                 445

Glu Met Ala Glu Leu Gly Pro Leu Asn Lys Tyr Leu Gln Gln Asn Arg
        450                 455                 460

His Val Lys Asp Lys Asn Ile Ile Glu Leu Val His Gln Val Ser Met
465                 470                 475                 480

Gly Met Lys Tyr Leu Glu Glu Ser Asn Phe Val His Arg Asp Leu Ala
                    485                 490                 495

Ala Arg Asn Val Leu Leu Val Thr Gln His Tyr Ala Lys Ile Ser Asp
                500                 505                 510

Phe Gly Leu Ser Lys Ala Leu Arg Ala Asp Glu Asn Tyr Tyr Lys Ala
            515                 520                 525

Gln Thr His Gly Lys Trp Pro Val Lys Trp Tyr Ala Pro Glu Cys Ile
        530                 535                 540

Asn Tyr Tyr Lys Phe Ser Ser Lys Ser Asp Val Trp Ser Phe Gly Val
545                 550                 555                 560

Leu Met Trp Glu Ala Phe Ser Tyr Gly Gln Lys Pro Tyr Arg Gly Met
                    565                 570                 575

Lys Gly Ser Glu Val Thr Ala Met Leu Glu Lys Gly Glu Arg Met Gly
                580                 585                 590

Cys Pro Ala Gly Cys Pro Arg Glu Met Tyr Asp Leu Met Asn Leu Cys
            595                 600                 605

Trp Thr Tyr Asp Val Glu Asn Arg Pro Gly Phe Ala Ala Val Glu Leu
        610                 615                 620

Arg Leu Arg Asn Tyr Tyr Tyr Asp Val Val Asn
625                 630                 635

<210> SEQ ID NO 4
<211> LENGTH: 537
<212> TYPE: PRT
<213> ORGANISM: Homo sapiens

<400> SEQUENCE: 4

Met Gly Cys Val Gln Cys Lys Asp Lys Glu Ala Thr Lys Leu Thr Glu
 1               5                  10                  15

Glu Arg Asp Gly Ser Leu Asn Gln Ser Ser Gly Tyr Arg Tyr Gly Thr
                20                  25                  30

Asp Pro Thr Pro Gln His Tyr Pro Ser Phe Gly Val Thr Ser Ile Pro
            35                  40                  45

Asn Tyr Asn Asn Phe His Ala Ala Gly Gly Gln Gly Leu Thr Val Phe
        50                  55                  60

Gly Gly Val Asn Ser Ser Ser His Thr Gly Thr Leu Arg Thr Arg Gly
65                  70                  75                  80

Gly Thr Gly Val Thr Leu Phe Val Ala Leu Tyr Asp Tyr Glu Ala Arg
                    85                  90                  95

Thr Glu Asp Asp Leu Ser Phe His Lys Gly Glu Lys Phe Gln Ile Leu
                100                 105                 110

Asn Ser Ser Glu Gly Asp Trp Trp Glu Ala Arg Ser Leu Thr Thr Gly
```

-continued

```
            115                 120                 125
Glu Thr Gly Tyr Ile Pro Ser Asn Tyr Val Ala Pro Val Asp Ser Ile
130                 135                 140

Gln Ala Glu Glu Trp Tyr Phe Gly Lys Leu Gly Arg Lys Asp Ala Glu
145                 150                 155                 160

Arg Gln Leu Leu Ser Phe Gly Asn Pro Arg Gly Thr Phe Leu Ile Arg
                165                 170                 175

Glu Ser Glu Thr Thr Lys Gly Ala Tyr Ser Leu Ser Ile Arg Asp Trp
                180                 185                 190

Asp Asp Met Lys Gly Asp His Val Lys His Tyr Lys Ile Arg Lys Leu
                195                 200                 205

Asp Asn Gly Gly Tyr Tyr Ile Thr Thr Arg Ala Gln Phe Glu Thr Leu
210                 215                 220

Gln Gln Leu Val Gln His Tyr Ser Glu Arg Ala Ala Gly Leu Cys Cys
225                 230                 235                 240

Arg Leu Val Val Pro Cys His Lys Gly Met Pro Arg Leu Thr Asp Leu
                245                 250                 255

Ser Val Lys Thr Lys Asp Val Trp Glu Ile Pro Arg Glu Ser Leu Gln
                260                 265                 270

Leu Ile Lys Arg Leu Gly Asn Gly Gln Phe Gly Glu Val Trp Met Gly
                275                 280                 285

Thr Trp Asn Gly Asn Thr Lys Val Ala Ile Lys Thr Leu Lys Pro Gly
290                 295                 300

Thr Met Ser Pro Glu Ser Phe Leu Glu Glu Ala Gln Ile Met Lys Lys
305                 310                 315                 320

Leu Lys His Asp Lys Leu Val Gln Leu Tyr Ala Val Val Ser Glu Glu
                325                 330                 335

Pro Ile Tyr Ile Val Thr Glu Tyr Met Asn Lys Gly Ser Leu Leu Asp
                340                 345                 350

Phe Leu Lys Asp Gly Glu Gly Thr Ala Leu Lys Leu Pro Asn Leu Val
                355                 360                 365

Asp Met Ala Ala Gln Val Ala Ala Gly Met Ala Tyr Ile Glu Arg Met
370                 375                 380

Asn Tyr Ile His Arg Asp Leu Arg Ser Ala Asn Ile Leu Val Gly Asn
385                 390                 395                 400

Gly Leu Ile Cys Lys Ile Ala Asp Phe Gly Leu Ala Arg Leu Ile Glu
                405                 410                 415

Asp Asn Glu Tyr Thr Ala Arg Gln Gly Ala Lys Phe Pro Ile Lys Trp
                420                 425                 430

Thr Ala Pro Glu Ala Ala Leu Tyr Gly Arg Phe Thr Ile Lys Ser Asp
                435                 440                 445

Val Trp Ser Phe Gly Ile Leu Leu Thr Glu Leu Val Thr Lys Gly Arg
                450                 455                 460

Val Pro Tyr Pro Gly Met Asn Asn Arg Glu Val Leu Glu Gln Val Glu
465                 470                 475                 480

Arg Gly Tyr Arg Met Pro Cys Pro Gln Asp Cys Pro Ile Ser Leu His
                485                 490                 495

Glu Leu Met Ile His Cys Trp Lys Lys Asp Pro Glu Glu Arg Pro Thr
                500                 505                 510

Phe Glu Tyr Leu Gln Ser Phe Leu Glu Asp Tyr Phe Thr Ala Thr Glu
                515                 520                 525

Pro Gln Tyr Gln Pro Gly Glu Asn Leu
530                 535
```

```
<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
cacgctggga cgttcgggtt gggggac                                           27

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
gtcccccaac ccgaacgtcc cagcgtg                                           27

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7 gatcagggggg gcttcaccat gcaccaag                                         28

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
cttggtgcat ggtgaagccc ccctgatc                                          28

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
gatcgcagcg gcttcagcag ccccgg                                            26

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
ccggggctgc tgaagccgct gcgatc                                            26

<210> SEQ ID NO 11
<211> LENGTH: 38
<212> TYPE: DNA
<213> ORGANISM: Artificial Sequence
<220> FEATURE:
<223> OTHER INFORMATION: Primer
```

<400> SEQUENCE: 11
ggcagtgtgc aaatagtctt caaaccagtt gacctgag    38

<210> SEQ ID NO 12
<211> LENGTH: 38
<212> TYPE: DNA
<213> ORGANISM: Artificial Sequence
<220> FEATURE:
<223> OTHER INFORMATION: Primer

<400> SEQUENCE: 12
ctcaggtcaa ctggtttgaa gactatttgc acactgcc    38

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13
gcggagatcg tgttcaagtc gccagtgg    28

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
ccactggcga cttgaacacg atctccgc    28

<210> SEQ ID NO 15
<211> LENGTH: 38
<212> TYPE: DNA
<213> ORGANISM: Artificial Sequence
<220> FEATURE:
<223> OTHER INFORMATION: Primer

<400> SEQUENCE: 15
ggcagtgtgc aaatagtcta caaaccagtt gacctgag    38

<210> SEQ ID NO 16
<211> LENGTH: 38
<212> TYPE: DNA
<213> ORGANISM: Artificial Sequence
<220> FEATURE:
<223> OTHER INFORMATION: Primer

<400> SEQUENCE: 16
ctcaggtcaa ctggtttgta gactatttgc acactgcc    38

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
gcggagatcg tgtacaagtc gccagtgg    28

<210> SEQ ID NO 18
<211> LENGTH: 28
<212> TYPE: DNA

```
<213> ORGANISM: Artificial Sequence
<220> FEATURE:
<223> OTHER INFORMATION: Primer

<400> SEQUENCE: 18
ccactggcga cttgtacacg atctccgc                                          28
```